(12) United States Patent
Wang et al.

(10) Patent No.: US 10,811,139 B1
(45) Date of Patent: Oct. 20, 2020

(54) COMPUTER NETWORK ARCHITECTURE WITH MACHINE LEARNING AND ARTIFICIAL INTELLIGENCE AND DYNAMIC PATIENT GUIDANCE

(71) Applicant: Clarify Health Solutions, Inc., San Francisco, CA (US)

(72) Inventors: Yale Wang, San Francisco, CA (US); Samuel H. Bauknight, San Francisco, CA (US); Adam F. Rogow, San Francisco, CA (US); Jeffrey D. Larson, San Francisco, CA (US); Jean P. Drouin, San Francisco, CA (US)

(73) Assignee: Clarify Health Solutions, Inc., San Francisco, CA (US)

( * ) Notice: Subject to any disclaimer, the term of this patent is extended or adjusted under 35 U.S.C. 154(b) by 175 days.

(21) Appl. No.: 16/007,819

(22) Filed: Jun. 13, 2018

(51) Int. Cl.
| | |
|---|---|
| *G16H 50/20* | (2018.01) |
| *G16H 50/30* | (2018.01) |
| *G06N 20/00* | (2019.01) |
| *G16H 80/00* | (2018.01) |
| *G16H 10/60* | (2018.01) |

(52) U.S. Cl.
CPC .............. *G16H 50/30* (2018.01); *G06N 20/00* (2019.01); *G16H 10/60* (2018.01); *G16H 50/20* (2018.01); *G16H 80/00* (2018.01)

(58) Field of Classification Search
CPC ........ G16H 50/30; G16H 10/60; G16H 50/20; G16H 80/00; G06N 20/00; G06N 5/05; G06N 7/00; G06N 99/00; G06F 19/00; G06F 17/30

USPC .......................................................... 705/2, 3
See application file for complete search history.

(56) References Cited

U.S. PATENT DOCUMENTS

| | | |
|---|---|---|
| 7,917,377 B2 | 3/2011 | Rao |
| 8,508,336 B2 | 8/2013 | Giobbi |
| 9,195,732 B2 | 11/2015 | Anderson |
| 10,127,234 B1 * | 11/2018 | Krishnan .............. G06F 16/119 |
| 2005/0137912 A1 | 6/2005 | Rao |
| 2005/0222867 A1 | 10/2005 | Underwood |
| 2006/0052945 A1 | 3/2006 | Rabinowitz et al. |
| 2006/0080139 A1 | 4/2006 | Mainzer |
| 2008/0183508 A1 | 7/2008 | Harker |
| 2009/0006419 A1 | 1/2009 | Savitsky |
| 2009/0206992 A1 * | 8/2009 | Giobbi .................. G06Q 10/10 340/5.74 |
| 2011/0213625 A1 | 9/2011 | Joao |
| 2011/0289035 A1 | 11/2011 | Stojadinovic et al. |
| 2012/0047105 A1 | 2/2012 | Saigal |

(Continued)

OTHER PUBLICATIONS

U.S. Appl. No. 15/845,633, filed Dec. 18, 2017.

(Continued)

*Primary Examiner* — Aryan E Weisenfeld
*Assistant Examiner* — Alaaeldin M Elshaer
(74) *Attorney, Agent, or Firm* — Akerman LLP; Stephen C. Glazier

(57) ABSTRACT

Embodiments in the present disclosure relate generally to computer network architectures for machine learning, artificial intelligence, and dynamic patient guidance. Embodiments automatically update patient guidance in the patient care plan, based on the effectiveness of the guidance to date, attributes of the patient, other updated information, ongoing experience of the network, and updated predictions of possible patient outcomes and metrics.

14 Claims, 14 Drawing Sheets

(56) References Cited

U.S. PATENT DOCUMENTS

| | | |
|---|---|---|
| 2012/0179478 A1 | 7/2012 | Ross |
| 2012/0271612 A1 | 10/2012 | Barsoum |
| 2013/0054259 A1 | 2/2013 | Wojtusiak |
| 2013/0096937 A1* | 4/2013 | Campbell ............... G06F 19/32 705/2 |
| 2013/0226624 A1 | 8/2013 | Blessman |
| 2014/0058763 A1 | 2/2014 | Zizzamia |
| 2014/0316810 A1 | 10/2014 | Oliver |
| 2015/0088541 A1 | 3/2015 | Yao |
| 2015/0095069 A1 | 4/2015 | Waljee |
| 2015/0100336 A1 | 4/2015 | Ford |
| 2015/0261922 A1 | 9/2015 | Nawana |
| 2016/0092641 A1 | 3/2016 | Delaney |
| 2016/0328526 A1 | 11/2016 | Park |
| 2017/0029894 A1 | 2/2017 | Damask |
| 2017/0140114 A1* | 5/2017 | Are ....................... G06N 20/00 |
| 2017/0236063 A1* | 8/2017 | Dorris .................. G06Q 50/22 706/11 |
| 2017/0293722 A1 | 10/2017 | Valverde, Jr. |
| 2017/0308650 A1 | 10/2017 | Brill |
| 2017/0308652 A1 | 10/2017 | Ligon |
| 2018/0060744 A1 | 3/2018 | Achin |
| 2018/0137247 A1 | 5/2018 | Bore |
| 2018/0182475 A1* | 6/2018 | Cossler .................. G16H 10/60 |

OTHER PUBLICATIONS

U.S. Appl. No. 15/998,771, filed Aug. 16, 2018.
Drouin et al., U.S. Appl. No. 16/584,326, filed Sep. 26, 2019.
Drouin et al., U.S. Appl. No. 16/373,316, filed Apr. 2, 2019.
Warner et al., U.S. Appl. No. 16/587,780, filed Sep. 30, 2019.
Gottula et al., U.S. Appl. No. 16/387,713, filed Apr. 18, 2019.
Talvola et al., U.S. Appl. No. 16/404,446, filed May 6, 2019.
Drouin et al., U.S. Appl. No. 16/533,465 filed Aug. 6, 2019.
Wang et al., U.S. Appl. No. 16/694,292, filed Nov. 25, 2019.
Larson et al., U.S. Appl. No. 16/694,330, filed Nov. 25, 2019.
Sheth et al., Active Semantic Electronic Medical Records, 5th Int'l Semantic Web Conference, Athens, GA, Nov. 6-Nov. 9, 2006.
Talvola et al., U.S. Appl. No. 16/697,773, filed Nov. 27, 2019.

* cited by examiner

COMPUTER NETWORK ARCHITECTURE WITH MACHINE LEARNING AND ARTIFICIAL INTELLIGENCE AND DYNAMIC PATIENT GUIDANCE

TECHNICAL FIELD

The present disclosure is related generally to computer network architectures for machine learning and artificial intelligence that enable a computer to learn by its own experience with users and by the passage of time, thus enabling computer hardware to perform better. Various embodiments apply to the healthcare field and constitute a healthcare robot with artificial intelligence.

BACKGROUND

There is a longstanding frustrated need to have programmable hardware function in a better manner, and particularly to have hardware be smarter and learn from its own experience, with machine learning and artificial intelligence.

The longstanding frustrated need is particularly acute in the healthcare field. Historically, patient care plans have been static. Patients undergoing medical procedures may have been given an educational binder with materials and checklists. But, if something is not covered in the documents, or if the patient does not adhere to the prescribed checklists, this prior art approach cannot adapt to bring the patient back on track with the patient care plan.

There is a frustrated need for a computer system with artificial intelligence and dynamic patient guidance to ensure patients are on track with the patient care plan. This would avoid the need for care coordinators to first call or e-mail patients to simply double check that everything is going well, rather than being able to focus their work on patients who are off track.

SUMMARY

The present disclosure is related generally to computer network architectures for machine learning and artificial intelligence that enable a computer to learn by its own experience with users and by the passage of time, thus enabling superior performance by the computer hardware. Various embodiments apply to the healthcare field and constitute a healthcare robot with artificial intelligence.

The present disclosure describes a computer network architecture with machine learning and artificial intelligence to allow for a patient's behavior and characteristics to continually inform and update how a patient is to be guided through their care plan, and how much expensive, direct intervention by care coordinators is required.

Embodiments automatically adapt patient guidance in the care plan based on the effectiveness of the guidance to date and attributes of the patient.

DESCRIPTION OF DYNAMIC PATIENT GUIDANCE WEB APPLICATION—LAYER 3

Figure 1:
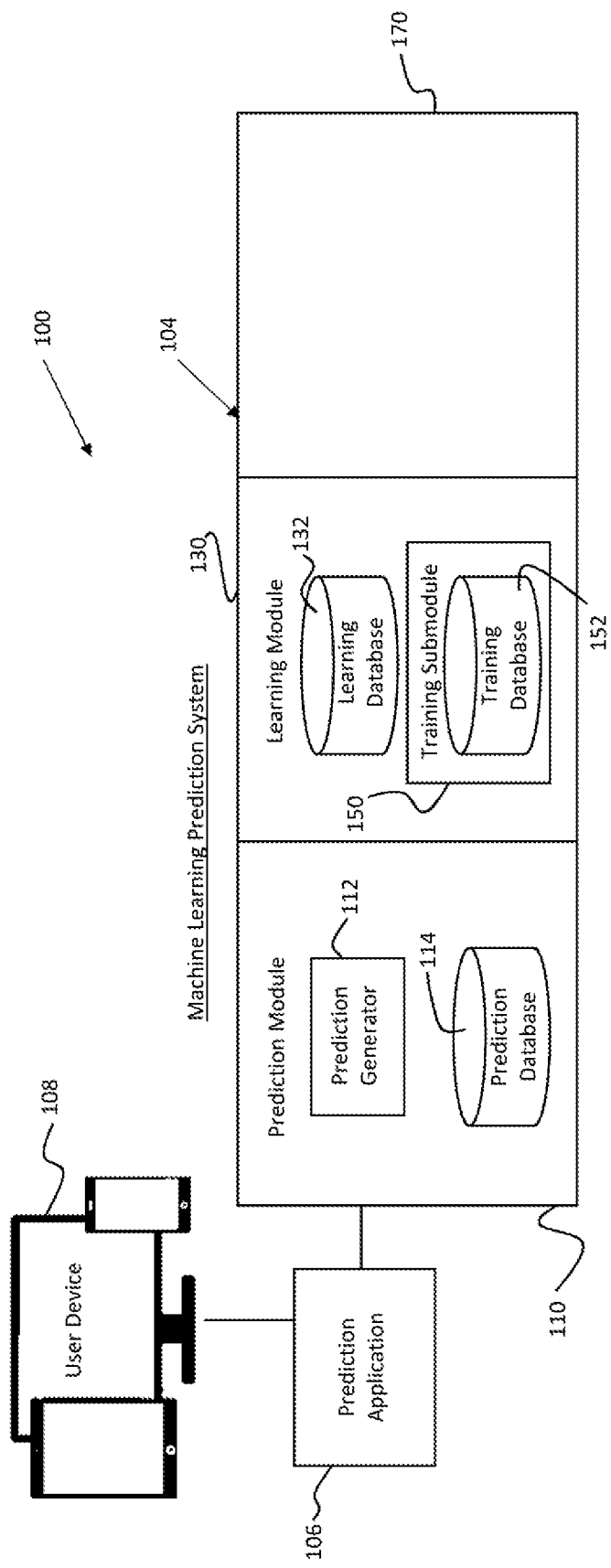
FIG. 1 schematically illustrates an overview of a computer network architecture including a machine learning system according to various embodiments described herein constituting healthcare robot hardware.

The present disclosure describes a computer network architecture with machine learning and artificial intelligence to allow for a patient's behavior and characteristics to continually inform and update how a patient is to be guided through their care plan, and how much expensive, direct intervention by care coordinators is required.

Embodiments automatically adapt patient guidance in the care plan based on the effectiveness of the guidance to date and attributes of the patient.

As patients use (or fail to use) an embodiment of the present invention, the present invention may track adherence to their prescribed care plan. Each important interaction causes the patient to be actively re-rated by the embodiment. The re-rating is in several dimensions, including, for example, likely cost, risk of readmission, and risk of dissatisfaction. As this rating changes, the content of the embodiment changes, and the guidance in the care plan is automatically updated based on the new ratings to keep the patient on track to optimize achievement of the care plan goals. The ratings are based on predictions of patient healthcare outcomes which are automatically made by the embodiment by its pipeline of healthcare outcome models with machine learning and artificial intelligence.

The following is an illustration example of the work flow of a user experience with an embodiment of a dynamic patient guidance web application (DPGWA), which is adapted to execute the following steps:

a. A patient logs into a Dynamic Patient Guidance Web Application (DPGWA) embodiment.
b. The patient interacts with the DPGWA software, updating the data in the architecture, about the patient behavior and/or compliance with the patient care plan. For example, the patient ignores an overdue check-in asking for key recovery progress indicators.
c. The patient logs out of the DPGWA.
d. The embodiment automatically re-rates the patient's ratings (i.e., re-scores the patient's risk scores) by accessing the patient risk scoring web application.
e. Based on the new ratings (i.e., new risk scores), the software of the embodiment changes the patient care plan.
f. The embodiment sends an automated message to the patient's mobile device requesting that the patient complete their check-in with the DPGWA and receive their updated patient care plan.
g. The embodiment creates a reminder task for the patient's clinical care coordinator to contact the patient, if the patient has not responded in, e.g., the next 24 hours.
h. If the patient has a designated caregiver, the embodiment sends a notification to the caregiver either (1) to prompt the patient to respond or (2) to respond on behalf of the patient to provide patient information.
i. If a patient adheres well to their care plan, embodiments of the present invention reduce the cadence of interventions by care coordinators for that patient.

An embodiment may include a computer network architecture with artificial intelligence and machine learning, comprising a prediction module with a prediction generator and an updated database; a learning module with a training submodule, in electronic communication with the prediction module and the updated database; a patient risk scoring web application in electronic communication with the prediction module and a user device; a dynamic patient guidance web application in electronic communication with the prediction module, the patient risk scoring web application; and a user device; and wherein the dynamic patient guidance web application is configured to log a patient into a the dynamic patient guidance web application (DPGWA); receive data from the patient; updating the data in the architecture; about the patient behavior and/or compliance with a patient care plan; log out the patient; automatically re-score the patient's risk scores by accessing the patient risk scoring web application; based on the new risk scores, update the patient care plan; send an automated message for the patient to the user mobile device requesting that the patient complete a check-in with the DPGWA and receive the updated patient care plan; create a reminder task for a patient clinical care coordinator to contact the patient, if the patient has not responded within a time period; if the patient has a designated caregiver, send a notification to the designated caregiver either (1) to prompt the patient to respond or (2) to respond on behalf of the patient to provide patient check-in information; and receive the updated patient care plan, and if the patient adheres well to their patient care plan, reduce the cadence of interventions by a care coordinator for that patient.

Three Layers

Embodiments of the present invention may be viewed as having an underlying data science layer. In the machine learning prediction system 104, this may be viewed as the first layer. This layer automatically adds new data streams (data capture) from all sources to the prediction database 114. This large expanding database contains all the data captured for all patients. The system makes predictions (e.g., the patient risk profile for a patient) based on the database. The predictions can be subtle with a large number of parameters and detailed demographic disaggregation of the patient groups.

The patient risk scoring web application 806,906 may be thought of as a second layer that operates on top of the first layer 104, making requests 190 to the first layer, and receiving responses 192 back.

A dynamic patient guidance web application (DPGWA) 1106 may operate on top of the second layer, as a third layer application.

Figure 11:
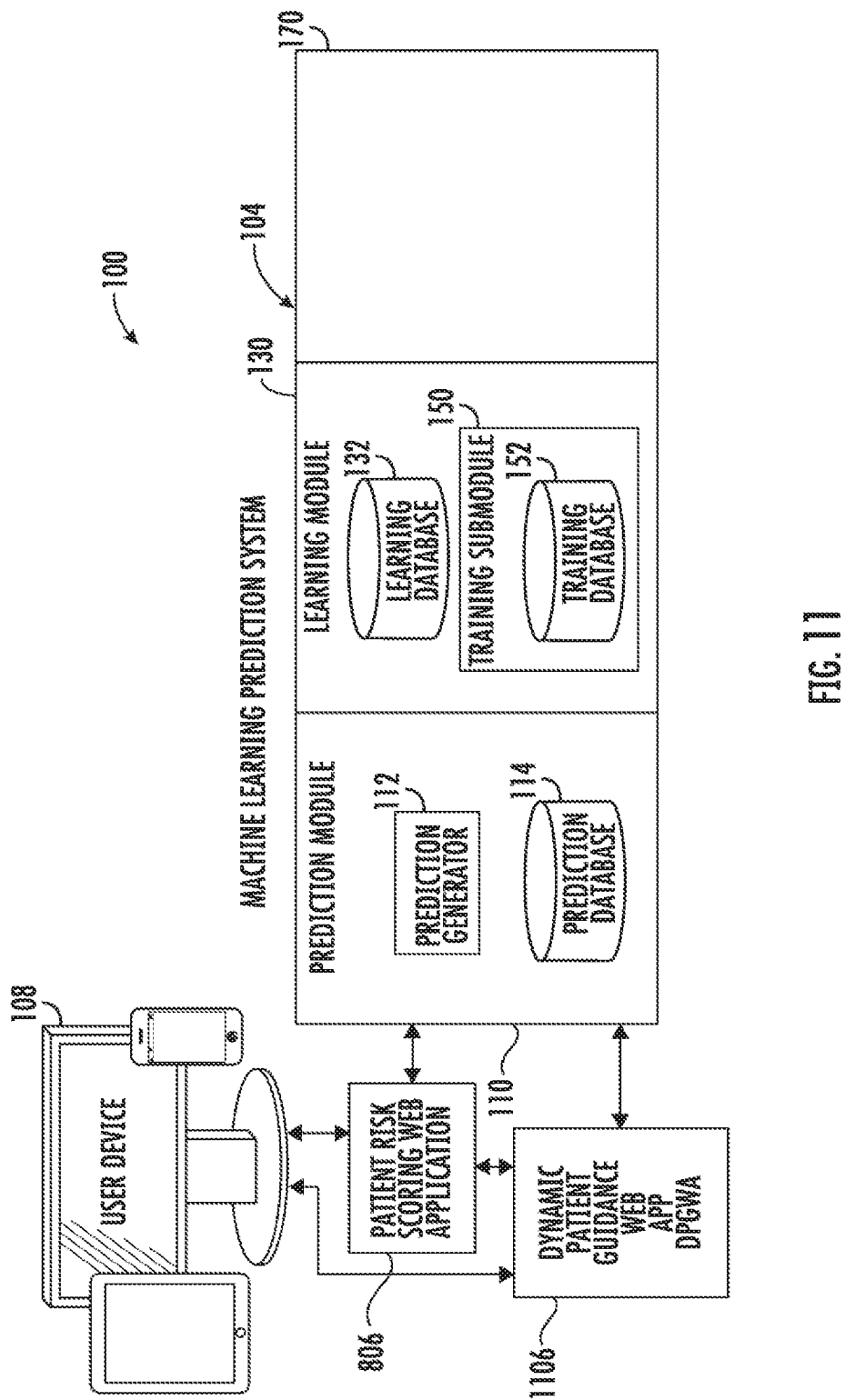
FIG. 11 schematically illustrates an overview of a computer network architecture including a machine learning prediction system and a web application configured to automatically generate data for a patient risk scoring and a web application configured to give dynamic patient guidance, according to various embodiments described herein.

FIG. 11 schematically illustrates an overview of a computer network architecture including a machine learning prediction system and a web application configured to automatically generate data for a patient risk scoring and a web application configured to give dynamic patient guidance, according to various embodiments described herein.

Figure 12:
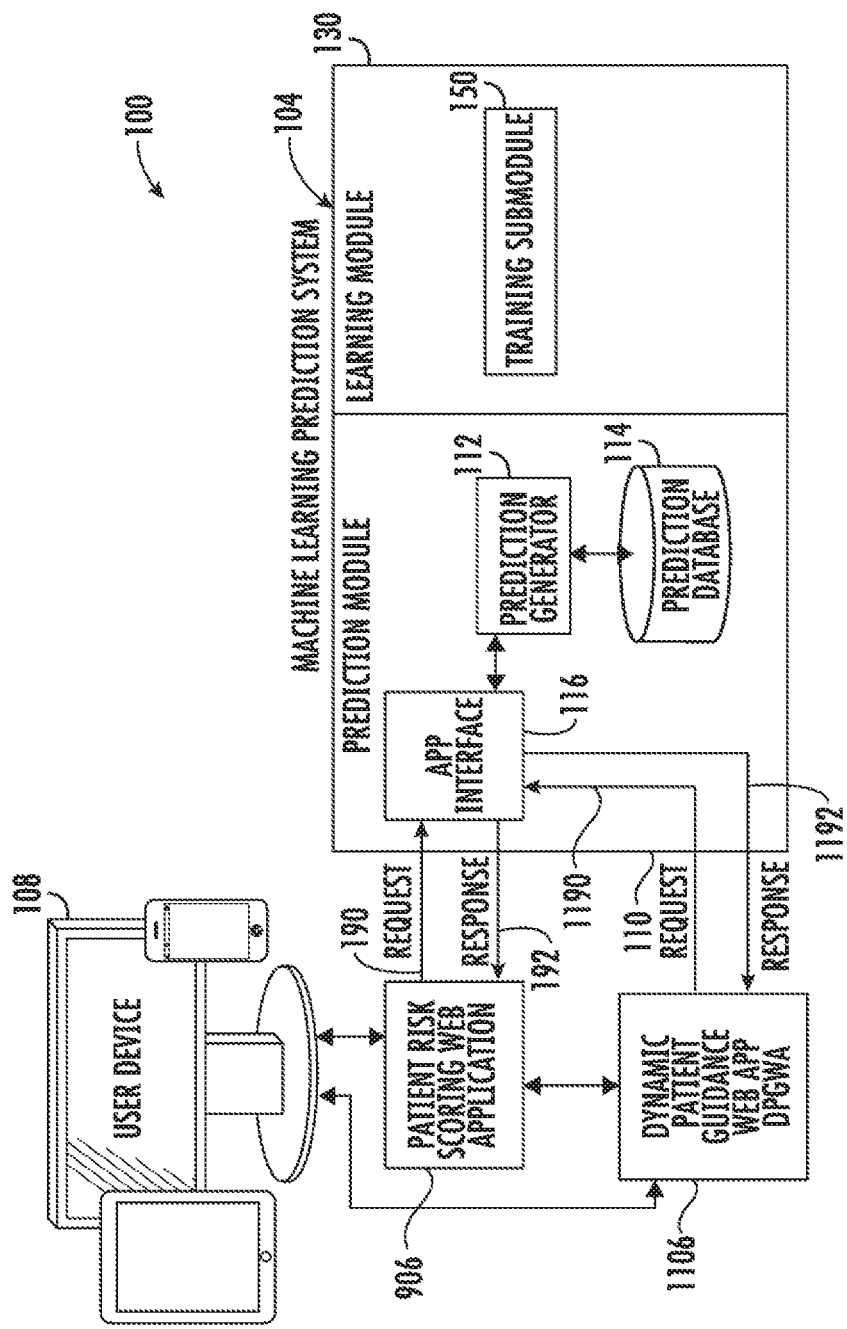
FIG. 12 schematically illustrates various aspects of a computer network architecture including a machine learning prediction system and a web application configured to automatically generate data for a patient risk scoring and a web application configured to give dynamic patient guidance, according to various embodiments described herein.

FIG. 12 schematically illustrates various aspects of a computer network architecture including a machine learning prediction system and a web application configured to automatically generate data for a patient risk scoring and a web application configured to give dynamic patient guidance, according to various embodiments described herein.

Figure 13:
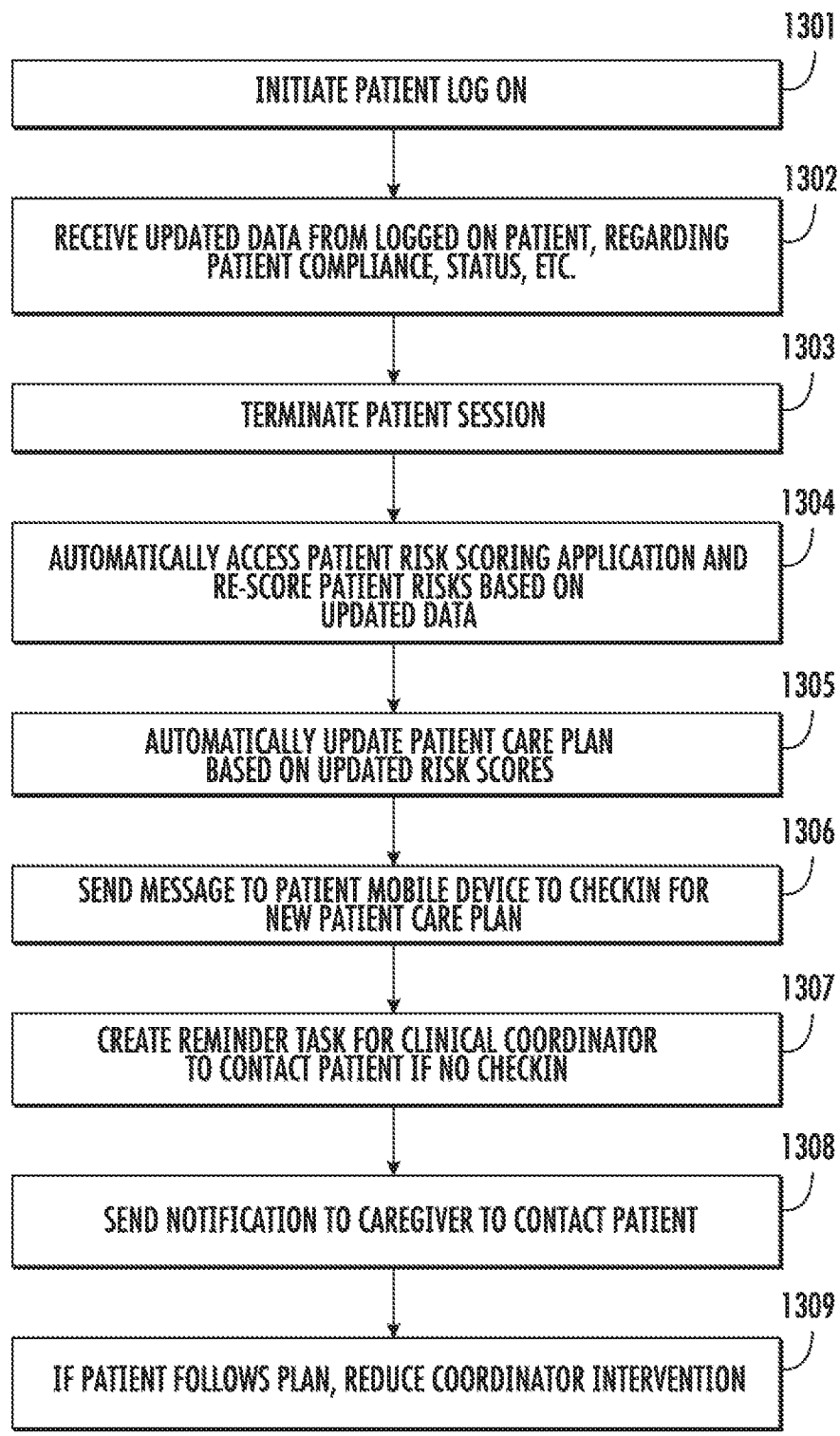
FIG. 13 is a process for a user experience with a dynamic patient guidance web application according to various embodiments described herein.

FIG. 13 is a process for a user experience with a dynamic patient guidance web application according to various embodiments described herein.

Figure 8:
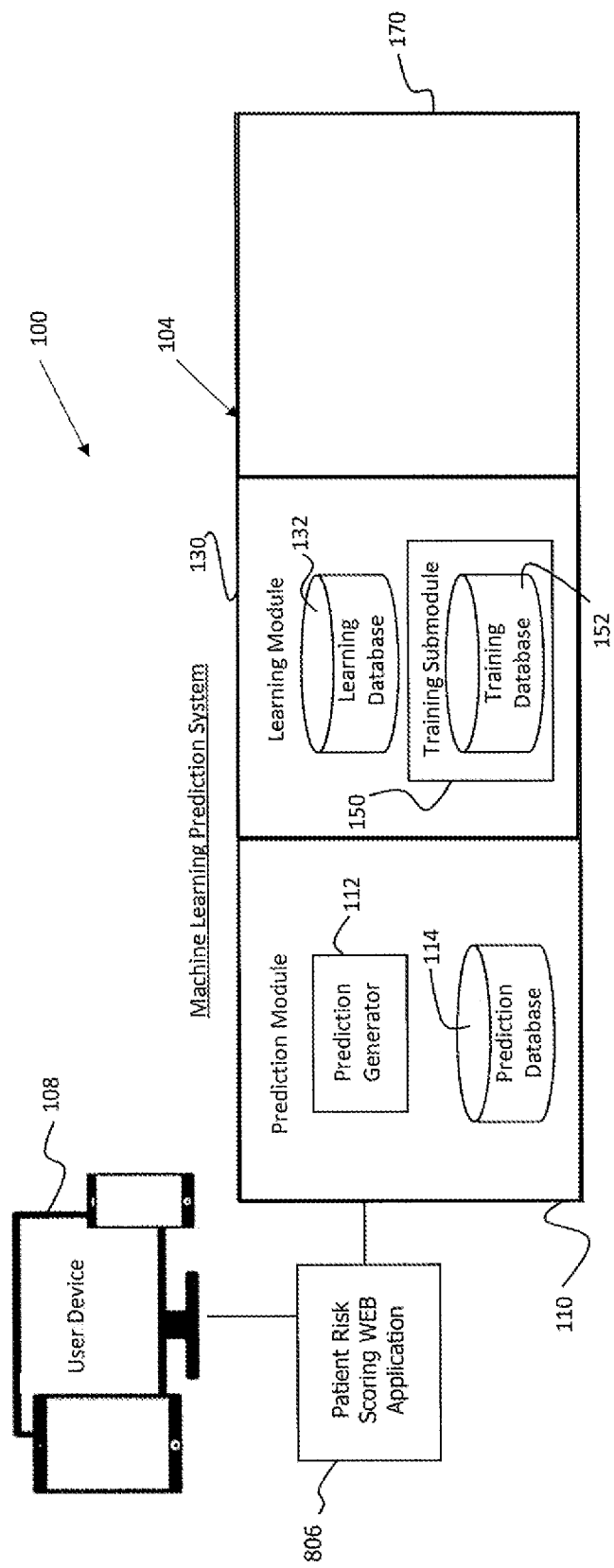
FIG. 8 schematically illustrates an overview of a computer network architecture including a machine learning prediction system and a web application configured to automatically generate data for patient risk scoring, according to various embodiments described herein.
Figure 9:
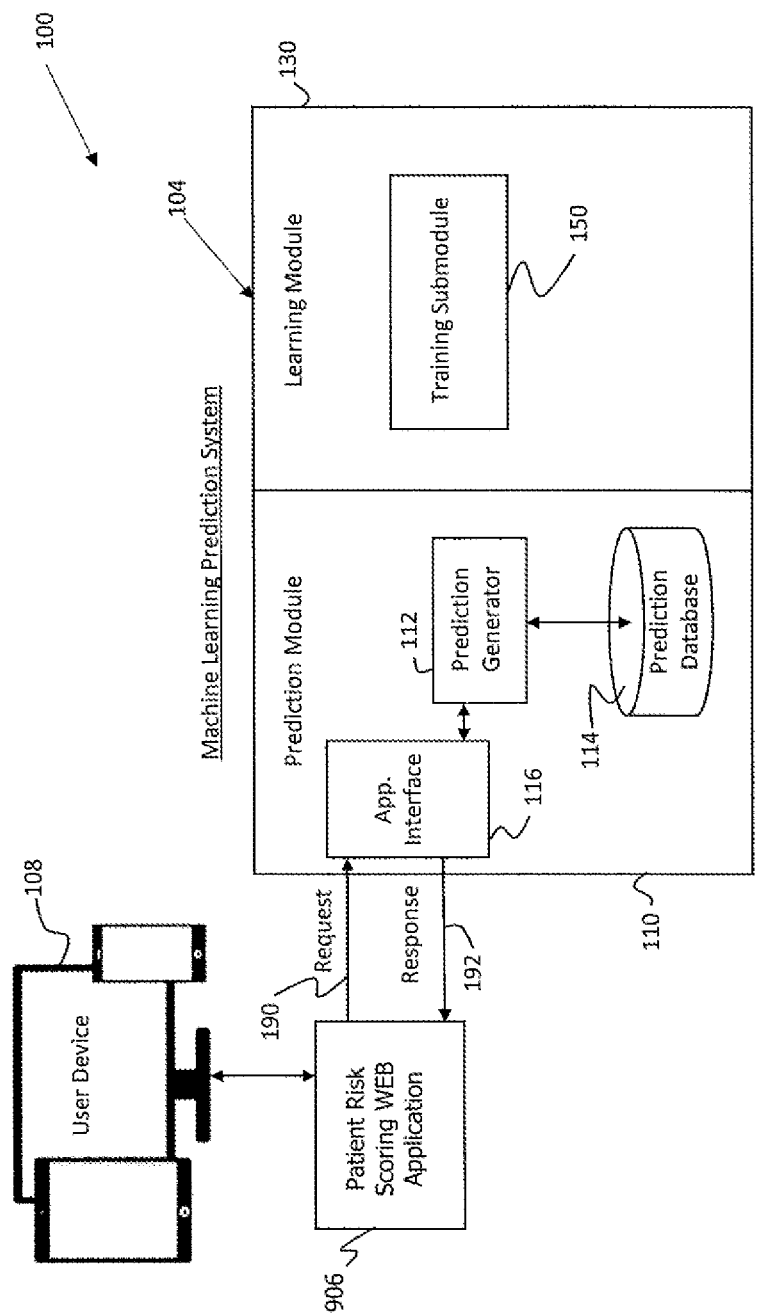
FIG. 9 schematically illustrates various aspects of a computer network architecture including a machine learning prediction system and a web application configured to automatically generate data for patient risk scoring, according to various embodiments described herein.

In various embodiments, the prediction application 106 in FIG. 1 and FIG. 9 may be embodied by dynamic patient guidance web application DPGWA 1106 and the patient risk scoring web application 806,906 in FIG. 11 and FIG. 12, components of which are further described in the discussion herein of related FIG. 8 and FIG. 9.

The process 1000 for the DPGWA 1106, according to various embodiments, is shown in FIG. 13. The DPGWA 1106 initiates the patient logon to the system 1301. The DPGWA 1106 receives 1302 updated data from the logged on patient, regarding patient compliance, status and other data. The DPGWA 1106 then terminates 1303 the patient logon session. DPGWA 1106 then automatically accesses the patient risk scoring application 806 and rescores 1304 the patient risks based on the updated data. Then the DPGWA 1106 automatically updates 1305 the patient care plan based on the updated risk scores. Step 1305 may automatically update the patient care plan based on the updated risk scores, by triggering a care plan reevaluation and care plan update by a manual consideration of the updated patient risk scores by clinical personnel, by notifying the personnel of the updated risk scores and the opportunity to reevaluate the care plan. The updated plan might alternatively be reevaluated and updated by an entirely automated algorithm, which may be within the journey engine 1405.

The DPGWA 1106 then sends 1306 a message to a patient mobile device to notify the patient to check in for the new patient care plan. The DPGWA 1106 then creates 1307 a reminder task for the clinical coordinator to contact the patient if there no patient check-in. The DPGWA 1106 then sends 1308 a notification to the caregiver to contact the patient. If the patient follows the care plan, the DPGWA 1106 reduces 1309 the cadence and frequency of the clinical coordinator intervention.

Automatically Updating 1304 the Patient Care Plan, and Generation of the Original Patient Care Plan An original patient care plan for an individual patient, may be produced automatically from the interpretable schedule generated 1005 by the risk scoring web application 806, 906, based on the patient risk scores, the customer rules, a menu of available care plan templates, payor plan rules, and individual patient data. The menu of available care plan templates, with possible tasks and actions for both the patient and the patient care team, is developed in concert with each customer that is provided an embodiment of the present invention by the vendor. The menu of available care plan templates is developed and updated by what the administrators of the system and their customers have learned by (1) working with previous customers and patients, (2) the insights developed by use of other components of the software suite of the vendor of the present system, regarding areas of potential performance improvement, and (3) the customer's own goals in using their embodiments with their patients (for example, goals regarding patient experience, communication, quality, cost, and patient satisfaction).

The patient care plan may be updated 1305 by the DPGWA dynamic patient guidance web application 1106, by recycling through the process by which the original patient care plan was developed, but with the updated patient risk scoring 1304, the updated patient data 1302 regarding patient compliance with the plan, and other information updated since the inception of the plan.

The menu of available patient care plan templates is developed by administrators of the system together with the customer, and is upgraded over time by administrators of the system and the customers, based on their continuing experience and collection of data.

The original patient care plan and the updated patient care plans may be automatically generated 1305 by the system. They may be manually approved by the customer when generated, or may be implemented without change.

The original patient care plan and the updated patient care plan may be automatically generated 1305 by logic within the prediction module 110, or by logic within the risk scoring web application 806, 906, or elsewhere within the system. But in any case, the patient care plans may be generated after the patient risk scores are developed 1304 by the patient risk scoring web application 806, 906.

Figure 14:
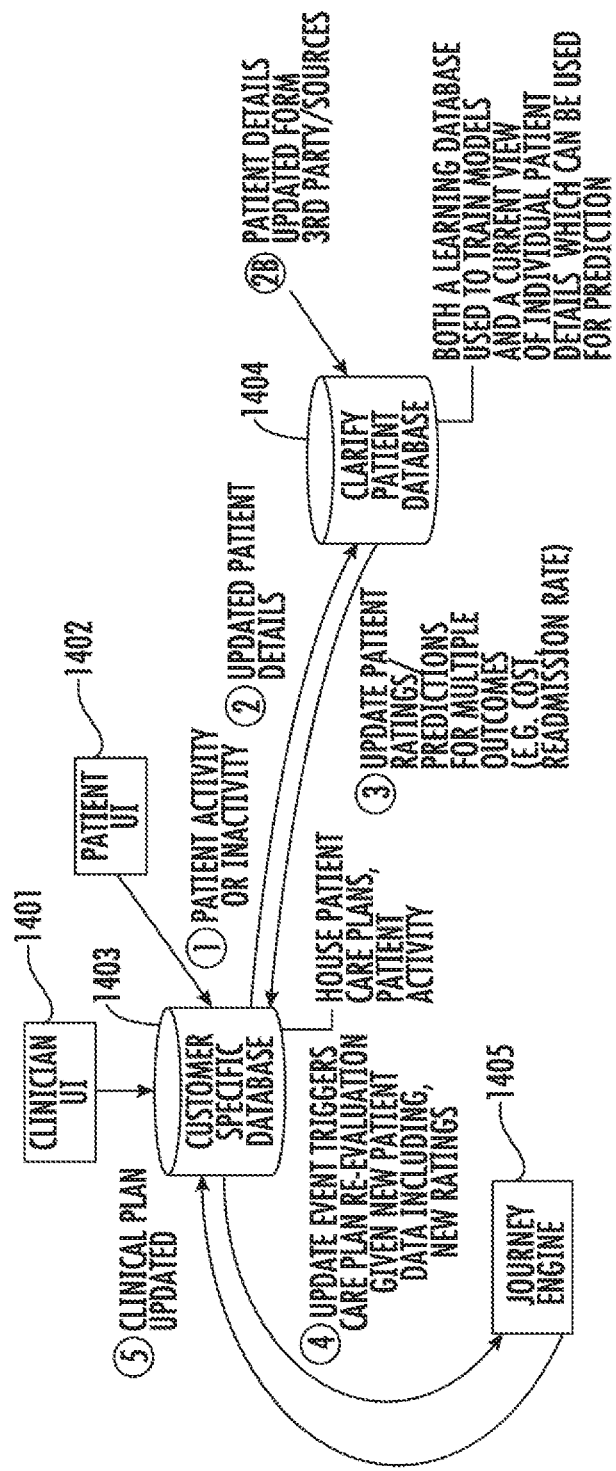
FIG. 14 is a flow diagram illustrating aspects of embodiments.

The "journey engine" 1405 in FIG. 14 denotes the methods and components disclosed in the patient risk scoring web application 806, 906, the dynamic patient guidance web application 1106, the prediction module 110, or elsewhere in the system, to produce and update the patient care plan, and its tasks and content for a given patient at a given time, as the patient passes through the patient care process (that is, during their "journey" through the patient care process).

FIG. 14 is a flow diagram illustrating aspects of various embodiments for further clarification. A clinician user interface 1401 may access the DPGWA 1106 and a patient user interface 1402 may access the DPGWA 1106. The clinician can thereby access a customer specific database 1403, and the customer specific database 1403 may thereby collect data on the patient activity or inactivity. The resulting data on updated patient details may then be transmitted by the system to the patient database 1404, sometimes referred to as Aristotle. The patient database 1404 may also receive detailed patient data updated on an ongoing basis from third-party sources such as insurance companies, healthcare providers, consumer financial data collectors and others. This database 1404 may be a learning database used to train models and a current view of individual patient details which can be used for prediction and risk scores by the prediction engine. The updated patient risk scores (ratings and predictions) for multiple outcomes may then be generated by the patient risk scoring application 806 (for example, predictions for an individual patient regarding costs, readmission rates, and other factors) and may be transmitted to a customer-specific database 1403. The customer-specific database 1403 may house patient care plans, patient activity, and other patient-specific information for patients associated with that specific customer. The update to the customer-specific database 1403 may then trigger patient care plan reevaluation, given the new patient data including the new ratings/risk scores from the patient risk scoring application 806. These updates may be done by reevaluation of the patient care plan in light of new data and predictions by human medical clinicians using a journey engine 1405. The updated patient care plan may then be transmitted back to the consumer-specific database 1403.

The customer specific database 1403 may be a distinct database within machine learning prediction system 104, or it may be part of the prediction database 114, or the training database 152 (for example, each patient in the database 114, 152 may be associated with a specific customer). The prediction database 114 may be distinct from the training database 152, or these two databases may be one database used for both prediction and training.

DESCRIPTION OF PIPELINE OF HEALTHCARE OUTCOME MODELS—LAYER 1

The present disclosure describes a novel network architecture configured to produce and automatically improve predictive models, particularly for patient healthcare outcomes regarding for example, cost, quality and patient satisfaction. According to various embodiments, the network architecture allows automatic machine learning as new data sources are added, and new data is collected, and the predictive algorithms are recalibrated and reselected using the expanded, and hence more reliable, data. This architecture addresses, for example, new waste identification problems in healthcare without having to proportionally increase labor cost. The above may enable users of the architecture to quickly realize the value of new data.

Utilization of the novel architecture described herein may enable more efficient operation, hosting, maintenance, integration and use of new data and data sources, and continuous automatic improvement of predictive models by recalibration and reselection of algorithms based on the expanding data.

Machine learning may incorporate predictive model algorithms to execute predictive analytical operations. Learning may be supervised or unsupervised. In general, a predictive model analyzes historical data to identify patterns in the data. The patterns identified may include relationships between various events, characteristics, or other attributes of the data being analyzed. Modeling of such patterns may provide a predictive model whereby predictions may be made. Development of predictive models may employ mathematical or statistical modeling techniques such as curve fitting, smoothing, and regression analysis to fit or train the data. Such techniques may be used to model the distribution and relationships of the variables, e.g., how one or more events, characteristics, or circumstances (which may be referred to as "independent variables" or "predictor variables") relate to an event or outcome (which may be referred to as a "dependent variable" or "response").

A machine learning process may include developing a predictive model. For example, a dataset comprising observed data may be input into a modeling process for mapping of the variables within the data. The mapped data may be used to develop a predictive model. The machine learning process may also include utilizing the predictive model to make predictions regarding a specified outcome that is a dependent variable with respect to the predictive model. The machine may then be provided an input of one or more observed predictor variables upon which the output or response is requested. By executing the machine learning algorithm utilizing the input, the requested response may be generated and outputted. Thus, based on the presence or occurrence of a known predictor variable, the machine learning algorithm may be used to predict a related future event or the probability of the future event.

The present invention applies generally to predictive algorithms informed by data. When the data relates to medical patients and treatments, and the algorithms correlate patient data with treatments and healthcare outcomes, then the system produces a pipeline of predictive models for healthcare outcomes that constantly improve and evolve with the machine learning and artificial intelligence of the present invention. For clarity and economy of description, the terms machine learning and artificial intelligence are often used interchangeably herein.

Machine Learning and Artificial Intelligence Architecture

FIG. 1 provides a schematic overview of a flexible computer network architecture 100 according to various embodiments. The network architecture 100 may include a machine learning prediction system 104. The machine learning prediction system 104 may be configured to generate machine learning algorithms comprising predictive models, automatically select and calibrate predictive models, build databases containing multiple predictive models for multiple model types as well as metrics for each model, add new databases to the system, build existing databases integrating new data, update system predictive models utilizing new data, receive prediction requests, and generate output responses comprising predictions based on input parameters via execution of the machine learning algorithms. As described in more detail below, the machine learning prediction system 104 may include one or more local or distributed hardware units comprising servers, communication devices, data storage devices, and processors configured to execute instructions for performing the operations of the machine learning prediction system 104.

The network architecture 100 may also include one or more prediction applications 106. In some embodiments, the prediction application 106 includes one or more web applications. The prediction application 106 or web applications thereof may include or access episode request templates for defining prediction requests. Prediction applications 106 may be generic for any end user, semi-generic, or customized for a single end user.

In one embodiment, the web applications (i.e., prediction applications), the prediction module, and the learning module may reside in the cloud and be administered by the invention's operator. Web applications may be structured for specific users, classes of users, templates or related data and predictions. In the healthcare industry, web applications may seek prediction reports for outcomes of specific patient episodes, and focus on factors such as patient guidance, automated healthcare performance benchmarks, estimates of missing clinical episode costs related to incomplete health insurance claims, patient risk scoring, forecasting episode and annual costs, facilities rating systems adjusted for risk, and other points.

In a healthcare embodiment, when an end user provides a request for a prediction report, the end user may give specific patient data (e.g., patient metrics and treatment) to populate a selected episode profile or template in a selected web application. The user requests a prediction report, e.g., a prognosis (i.e., predicted outcomes). Other web applications may give other reports. e.g., possible treatments, probability of each possible result of each treatment choice, economics, and schedule of prognosis and treatment. The web application then automatically accesses the prediction module and transmits the episode data with the request, and receives back a prediction report from the prediction module.

Prediction applications 106 may be configured to interface one or more user devices 108 with the machine learning prediction system 104. The user device 108 may access or run the prediction application 106, which may be stored locally, remotely, or reside in the cloud. For example, the user device 108 may remotely access the prediction application 106 with a browser through a network connection, such as an Internet, extranet, or VPN connection. User devices 108 may include an electronic communication device such as a computer, laptop, PDA, tablet, wearable computing device, or smart phone. The user device 108 will typically function as an end point with respect to the network architecture 100 and interface users with the network architecture 100. Users may include customer or client end users, which may be in a commercial environment such as in a SaaS environment. In an example healthcare application, a user or user device 108 may be associated with a customer or customer grouping, which may be a specific hospital, doctor office, insurance company, or grouping of multiple hospitals, doctor offices, or insurance companies, for example.

The machine learning prediction system 104 may include a prediction module 110 and a learning module 130. The prediction module 110 may include a prediction generator 112 configured to process prediction requests and generate prediction responses with respect to specified outcomes. For example, prediction requests, which may also be referred to as report requests, may include episode data comprising observed data related to a response variable. Using the episode data, the prediction generator 112 may execute machine learning algorithms comprising prediction models stored in a prediction database 114.

The learning module 130 may be configured to execute computer learning tasks including generating, calibrating, updating and evaluating system prediction models. The learning module 130 may include a training submodule 150 configured to execute training functions, which may include executing training requests, to fit data comprising observed episode data to one or more model types defined in the machine learning prediction system 104.

The machine learning prediction system 104 may include one or more databases, each of which may comprise one or more member databases, for storing episode data, metrics, model types, current best predictive models, archived predictive models, and other data from which the machine learning prediction system 104 may access to perform system operations. For example, the training submodule 150 may include a training database 152 that stores observed episode data for training system prediction models. The training database 152 may collect and accumulate data over time for use by the training submodule 150. In a healthcare application, for example, the training database 152 may include data relating to individual patients, episodes, and outcomes. In some embodiments, the training database 152 includes a customer's institutional data, which the training submodule 150 may access. In one embodiment, the customer's institutional data is restricted to us only for the customer. The training database 152 may also third party databases that may be used by the training submodule 150 to generate, update, or recalibrate system predictive models. Thus, the training submodule 150 may access or integrate third party databases. In some embodiments, the training database 152 includes one or more database repositories for medical data and socioeconomic data such as financial credit histories from credit rating companies. The training database 152 may reside in a single or multiple locations, be local or distributed, and may include third party databases accessible by the learning module 130 or training submodule 150. In one embodiment, the training database 152 may be divided or physical or logically partitioned into episode specific data libraries.

A library of system prediction models and associated metrics generated by the training submodule 150 may be stored in a learning database 132. The library may be used for evaluation of the archived models. For example, the learning database 132 may include multiple generated predictive models types of each of a plurality of specific episodes types. The learning module 130 may periodically or upon the occurrence of a predefined event, such as addition of new data or generation of new predictive models, compare metrics across the predictive models in the library to determine if a predictive model for a specific episode performs better than the predictive model for the episode that is stored in the prediction database 114, which the prediction module 110 currently uses for responding to prediction requests for the episode. If, based on the metrics comparison, the learning module 130 determines that another predictive model performs better than the one stored in the prediction database 114, the learning module 130 may replace the predictive model with the model determined to be the current best. The learning database 132 may maintain a record of the metrics and associated predicative models for future evaluations. In some embodiments, the learning module 130 may test or update the regression calibration of one or more algorithm to be used, and add episode data to the database to be kept and expanded and used by this and all subsequent queries.

In various embodiments, the network architecture 100 or machine learning prediction system 104 may also include an administration module 170. The administration module 170 may be configured to allow systems administrators to develop and control the machine learning prediction system 104, such as defining episode types. For example, system administrators may define patient episode types such as types of patient conditions to be handled, their metrics, and training databases 152 used. The machine learning prediction system 104 may be employed for machine learning and predictive analysis for any episode type. Episode types may include, for example, "hip and knee replacements under Medicare rules" or "pneumonia under Aetna Insurance" rules. The administration module 170 may provide, incorporate, or update episode type definitions, e.g., types of patients, metrics and parameters, and illness types. The administration module 170 may also allow system administrators to define which training database 152 or prediction database 114 each episode type will use. In some embodiments, system administrators may utilize the administration module 170 to add or integrate additional databases into the training databases 152, which may include third party databases. In the above or another embodiment, system administrators may utilize the administration module 170 to define which data each patient episode profile type will use. For example, utilizing the administration module 170, system administrators may define which parameters or attributes, such as predictor variables, associated with observed episode data is to be used for generating predictive models or predictions for specific episode types. An administrative application (see, e.g., FIG. 2) may also be used in addition to or instead of an administration module 170.

Further Network Architecture

Figure 2:
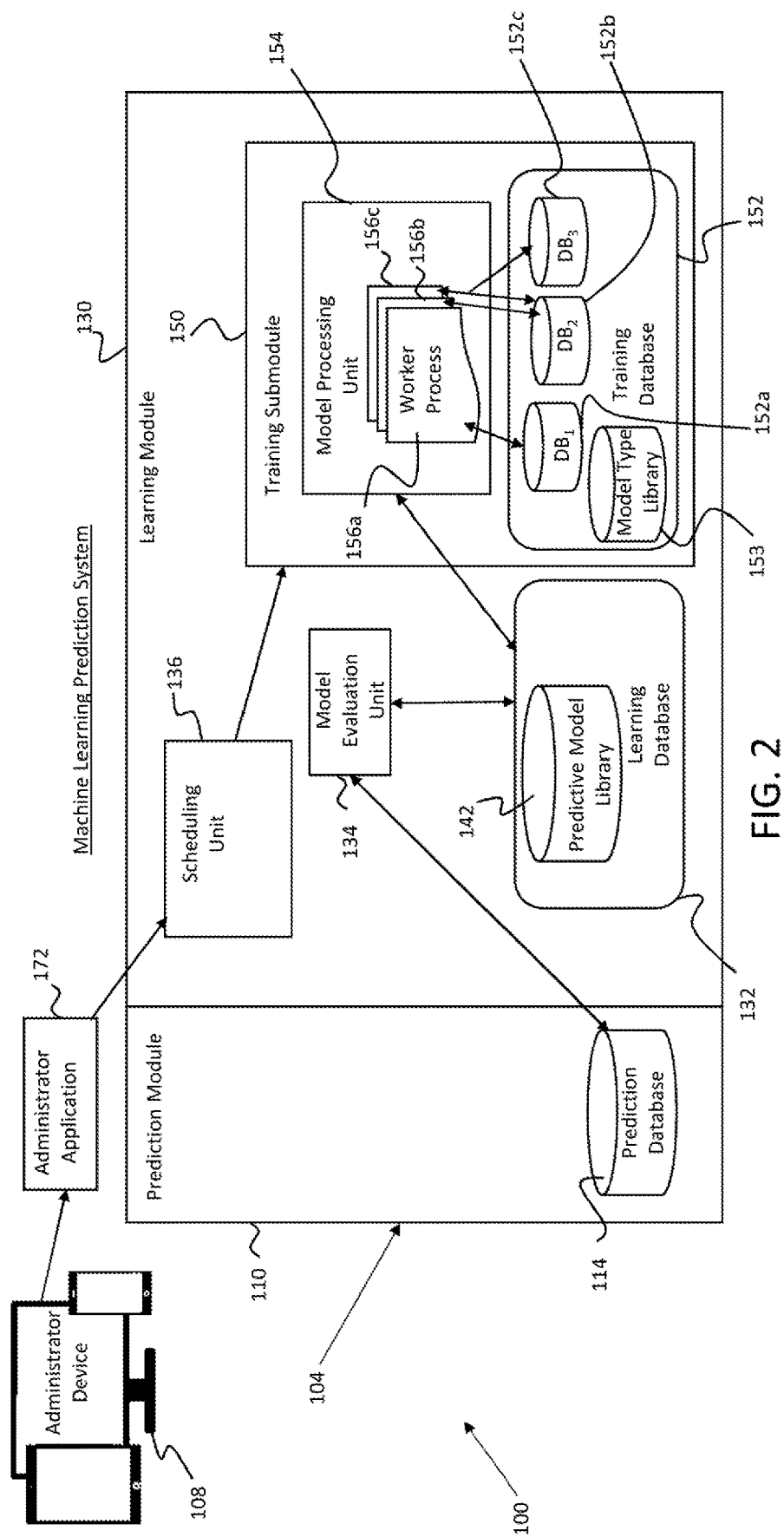
FIG. 2 schematically illustrates various aspects of a computer network architecture including a machine learning system according to various embodiments described herein.

FIG. 2 illustrates an embodiment of the computer network architecture 100 and machine learning prediction module 104 performing a machine learning operation including one or more of training, evaluation, storage, or management of prediction functions. In particular, the learning module 130 may be configured to execute a machine learning process wherein episodes, such as clinical episodes, are built and continually updated in the learning and training databases 132, 152, which represent the confluence of program specific episode logic and actual care provided to large populations of patients.

As introduced above with respect to FIG. 1, the learning module 130 may include or access a training database 152, which may include episode specific data libraries 152*a*, 152*b*, 152*c*, from which a training submodule 150 may draw upon to generate or train system predictive models. In some embodiments, the training database 152 includes third party or customer specific databases. Operation of the training submodule 150 may utilize actual observed data in the training database 152 to generate predictive models and associated metrics for inclusion in a predictive model library 142 of the learning database 132. It will be appreciated that episode specific data libraries 152*a*, 152*b*, 152*c* may be distributed among multiple hardware and locations. For example, episode specific library 152*a* may be distributed on or among one or more hardware locations, which may include one or more third party databases or customer databases. Episode specific library 152*b* may similarly be distributed on or among one or more hardware locations, which may or may not include one or more hardware locations including episode specific library 152*a*.

The learning module 130 or training submodule 150 thereof may include a model type library. In the illustrated embodiment, the training database 152 includes a model type library 153. In various embodiments, model types (sometimes referred to as algorithms) may include one or more of multi-level models, random forest regression models, logistical regression models, gamma-distributed regression models, linear regression models, or combinations thereof. Other model types may be used. In one embodiment, the learning module 130 may be configured to expand utilization of additional model types or redefine or update current model types.

In various embodiments, the learning mode 130 may be configured to automatically, such as periodically or upon the occurrence of a system event, generate training requests. For example, system events may include addition of accessible episode data corresponding to specific episodes, such as addition of or updating of data in the training database 152. The learning module 130 may generate training requests that include all, multiple, or portions of one, more, or all datasets in an episode specific training database 152*a*, 152*b*, 152*c*. For example, the learning module 130 may include a scheduling unit 136 configured to automatically initiate a training process to test or update calibration of the predictive models. For example, training may be initiated with each query, number or volume of queries, periodically, upon introduction of new data, or other time period or event.

In some embodiments, system administrators may submit requests to the learning module 130 instead of or in addition to automatic request generation. In the illustrated embodiment, an administer device 109 interfaces with the scheduling unit 136 via an administrator application 172 to initiate the training process. The administrator device 109 may access or run the administrator application 172, which may be stored locally, remotely, or reside in the cloud. In one embodiment, the administrative application 172 comprises a web application remotely accessible by the administrator device via a browser through a network connection, such as an Internet, extranet, or VPN connection. The administrator device 109 may include an electronic communication device such as a terminal, computer, laptop, PDA, tablet, or smart phone. The training request initiated by the administrator device 109 via the administrator application 172 may include a request template providing a model definition and dataset.

The model definition may identify parameters and episode attributes to use for model fitting in the training process. The dataset may include observed episode data including attribute values of predictor variables and response variables. In some embodiments, the dataset provided in the request may identify all or a portion of episode data stored in the training database 152 for the episode type that corresponds to the model definition, which may be in addition to or instead of transmission of new data in the request.

As introduced above, the dataset may include observed episode attribute values from a plurality of episodes corresponding to the episode type indicated in the model definition. For example, the model definition may specify post-op knee replacement prognosis (Y) and identify attributes, e.g., age, weight, education, income, hospital location, procedure variation, or other attributes (X), to be used in the modeling. The dataset may then include a plurality of data points comprising episode attribute values $y_0, x_{01} \ldots x_{0n}$, corresponding to the model definition. In various embodiments, multiple pairs of model definitions and datasets may be submitted to the training submodule 150, e.g., a list of requests comprising pairs of model definitions and datasets.

In various embodiments, the model definition may be generic to multiple types of models in the model type library 144. For example, the model definition may be applicable to two, more, or all types of models or category of types of models corresponding to an episode type. The model definition may directly or indirectly identify applicable model types. Alternatively or additionally, the learning module 130 may be configured such that model definitions are assumed to be applicable to all system model types unless indicated otherwise.

The training submodule 150 may include a model processing unit 154 configured to process training requests and generate predictive models according to the requests. The model processing unit 154 may employ one or more worker processes 156a, 156b, 156c to generate a fitted model, per the parameters of the request. Worker processes 156a, 156b, 156c may include modeling software programs, software functions, processes, or subroutines, for example. The model processing unit 154, or worker processes 156a, 156b, 156c thereof, may access the model type library 153 to obtain executable instructions for generating one or more predictive models for one or more of the model types using the dataset specified in the request.

In various embodiments, the model processing unit 154 may farm each model definition/dataset pair to a worker process 156a, 156b, 156c to generate fitted models. In one example of the training process, one or more worker process 156a, 156b, 156c may each be tasked with generating a fitted model, per the parameters of the request. As introduced above, the machine learning prediction system 104 may be configured to generically support multiple types of models. Accordingly, multiple fitted models may be generated corresponding to one or more model types. In some embodiments, each worker process 156a, 156b, 156c may run a script, such as a Python script, to generate respective fitted models. In one embodiment, worker processes 156a, 156b, 156c may access or be provided data specified in the request comprising one or more datasets or portions thereof from one or more specified episode specific training databases 152a, 152b, 152c. Alternately, worker processes 156a, 156b, 156c may be provided new or additional data identified by or included in the dataset of the training request. For example, the new or additional data may be accesses or obtained from a third party database. In some instances, all or a portion of the new or additional data may be retained and stored in the training database 152 and thereby expand available episode data for future fine tuning of the system's 104 episode modeling algorithms.

As introduced above, the model processing unit 154 may test generated predictive models, the metrics of which may be stored in the learning database 132. In the illustrated embodiment, the worker processes 156a, 156b, 156c test the fitted models generated from the episode definition/dataset pair in the request. The testing process may include one or more metric evaluations or other testing or evaluation schemes. In one example, worker processes 156a, 156b, 156c may perform k-fold cross-validation to estimate prediction ability of the generated fitted models. In a further example, k-fold cross-validation may include testing of a model via 5-fold cross-validation. K-fold cross-validation may include partitioning a dataset into k different partitions or folds. Fitting the model may therefore include training k−1 subsets as training data consistent with a model type and then testing the trained model with the remaining subset as a validation or test data. This may be repeated until all k subsets have been used as the validation or test data. Calculated cross-validation errors across the folds may be averaged. K-fold cross-validation may also be used to select the fitted model that is likely to be the most predictive with out-of-sample data.

The results of the model fitting and testing may be calculated by the model processing unit 154. For example, worker processes 156a, 156b, 156c may calculate evaluation metrics descriptive of the generated models, which may be used to compare models. Evaluation metrics may include, for example, one or more metrics selected from RMSE, mean bias, mean absolute error, area under the curve on a receiver operating characteristic plot, or combinations thereof. Other evaluation metrics may be used. For example, suitable evaluation metrics may be selected that correspond to the model task or design such as binary classification, multiclass, or multi-label (ROC, Cohen's Kappa, confusion matrix, MCC, accuracy classification score, F1 score, F-beta score, average Hamming loss, Jaccard similarly coefficient score). The results of the model fitting and testing may be captured in a learning database 132. The status of each model fitting worker process 156*a*, 156*b*, 156*c* may also be logged centrally, along with the status of the overall request process.

The learning module 130 may also include a model evaluation unit 134 configured to evaluate generated models in the predictive model library 142. For example, an RMSE, mean bias, mean absolute error, area under the curve on a receiver operating characteristic plot, and a date-time of model fit for each generated predictive model may be sent to the learning database 132 and stored in the predictive model library 142. The model evaluation unit 134 may use this captured test data to screen the predictive quality of the model versus captured test data of previous model versions applicable to a corresponding episode type, which may include comparisons across model versions within a model type or within multiple model types. If the model passes this screening, the model evaluation unit 134 may automatically incorporate the model into the prediction database 114 for use moving forward for future customer environments as the current best, or best-of-class, model for the corresponding episode type or possibly additional episode types.

The learning module 130 may be configured to periodically or upon occurrence of a predefined event test prediction accuracy of models in the predictive model library 142 against new, current, or existing episode data. For example, episode data may be dated in the training database to track currentness of the data to test ability of generated predictive algorithms to predict responses based on current episode data. Periodic prediction analysis may address drift, concept drift, or unintended honing or targeting of the model algorithm over time. Current or new episode data may also be obtained from a third party database or may be submitted in a request or imported into or associated with the training database 152, which may be an event that initiates analysis or evaluation of one or more system models, which may include best models, models that are not classified as current best models, or combinations thereof. A low calculated prediction accuracy may initiate retraining, updating, recalibration, or replacement of a current best model with a better performing model from the predictive model library 142 or a newly generated model fit and tested as above from new or existing episode data.

Accordingly, the machine learning prediction system 104 may be configured for machine learning and artificial intelligence during actual use by constant automatic fine-tuning of the calibration of the algorithm and expansion of the databases. The learning module 130 may test or update the regression calibration of system algorithms in the prediction database 114 and predictive model library 142 and add episode data to the training database 152 to be kept and expanded and used by subsequent queries.

Machine Learning Architecture

Figure 3:
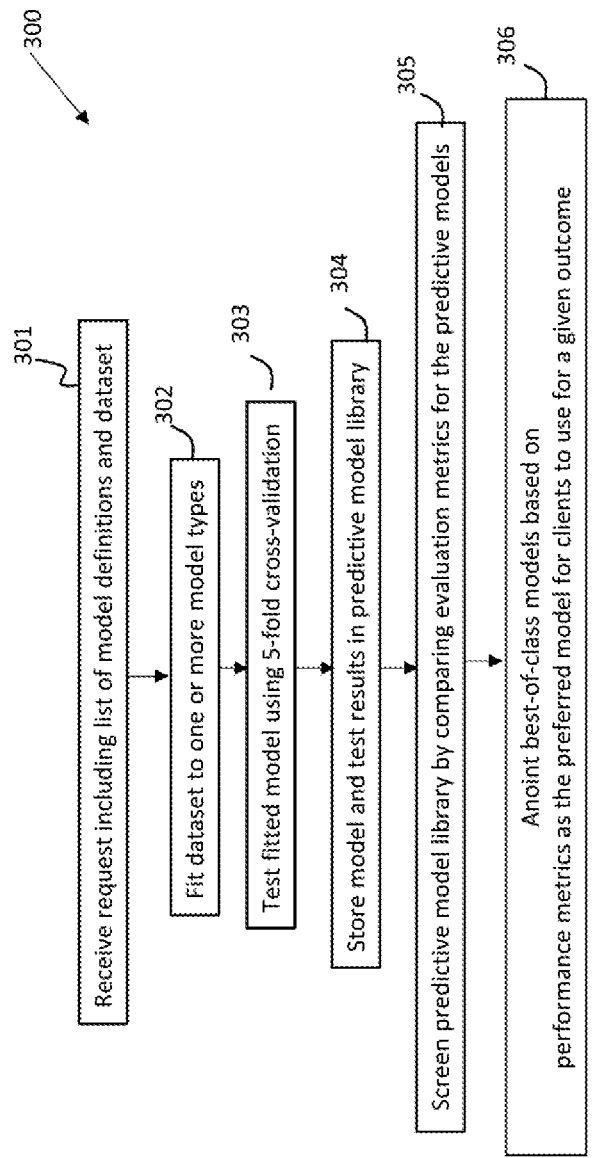
FIG. 3 is a prediction process of a computer network architecture including a machine learning prediction system according to various embodiments described herein.

FIG. 3 illustrates a training process 300 that may be utilized by the machine learning prediction system 104 (see, e.g., FIGS. 1 & 2) according to various embodiments. The training process 300 may include receiving a user request that includes a list of model definitions and a dataset 301, which may be similar to the request described with respect to FIG. 2. The dataset may then be fitted to one or more model types 302. For example, the training submodule may fit the dataset to one or more models types, that is, a plurality of predictive model algorithms may be calibrated by the available data set. The model types, or predictive algorithms, may include multi-level models, random forest regression models, logistical regression models, gamma-distributed regression models, linear regression models, combinations thereof, or other types. The fitted models (i.e., calibrated algorithms) may then be tested by a 5-fold cross-validation 303, although, in some embodiments, the fitted model may be tested using other testing techniques. The models and the test results may be stored in the predictive model library 304. The test results may include, for example, one or more of five cross-validation evaluation metrics selected from RMSE (root means square error), mean bias, mean absolute error, area under the curve on a receiver operating characteristic plot, or date-time of model fit. The models in the predictive model library, which may include models currently being used by the prediction module for servicing client requests, may be screened by comparing the evaluation metrics 305. Next, the screening results may be used to identify the best current model for a given response (that is, the algorithm with the best evaluation metrics after calibration with the current data is the best current algorithm), and that model may be anointed best-of-class model based on the performance metrics, that is, the preferred model for clients to use for a given outcome 306. Thus, if the screen indicates that a predictive model in the prediction model library performs better than a model currently being used by the prediction module for servicing the customer requests, the newly anointed best-of-class model may replace that model as the model used by the prediction module for servicing the customer request for the corresponding given response outcome.

The data used to calibrate, evaluate and select the algorithms (i.e., the models) is constantly updated by addition of applicable databases from users, and from third-party vendors, such as hospitals, medical practices, insurance companies, credit scoring agencies, and credit history agencies. Also, the data available is updated by the data from each user request for an individual prediction for a patient episode. The accumulating data continually expands over time and shall become an increasingly valuable asset. The training module may be automatically rerun periodically, occasionally, or with each individual user request for an individual prediction. That is, the algorithms may be automatically recalibrated, re-evaluated and reselected periodically, occasionally, or otherwise, using the then current expanding database. More data is more statistically reliable, so automatically re-running of the training module with more data makes the model predictions increasingly better, that is this machine learning is improving the prediction results. This provides an automatic artificial intelligence pipeline of ever-improving predictive models.

Network Architecture with Web Applications

Figure 4:
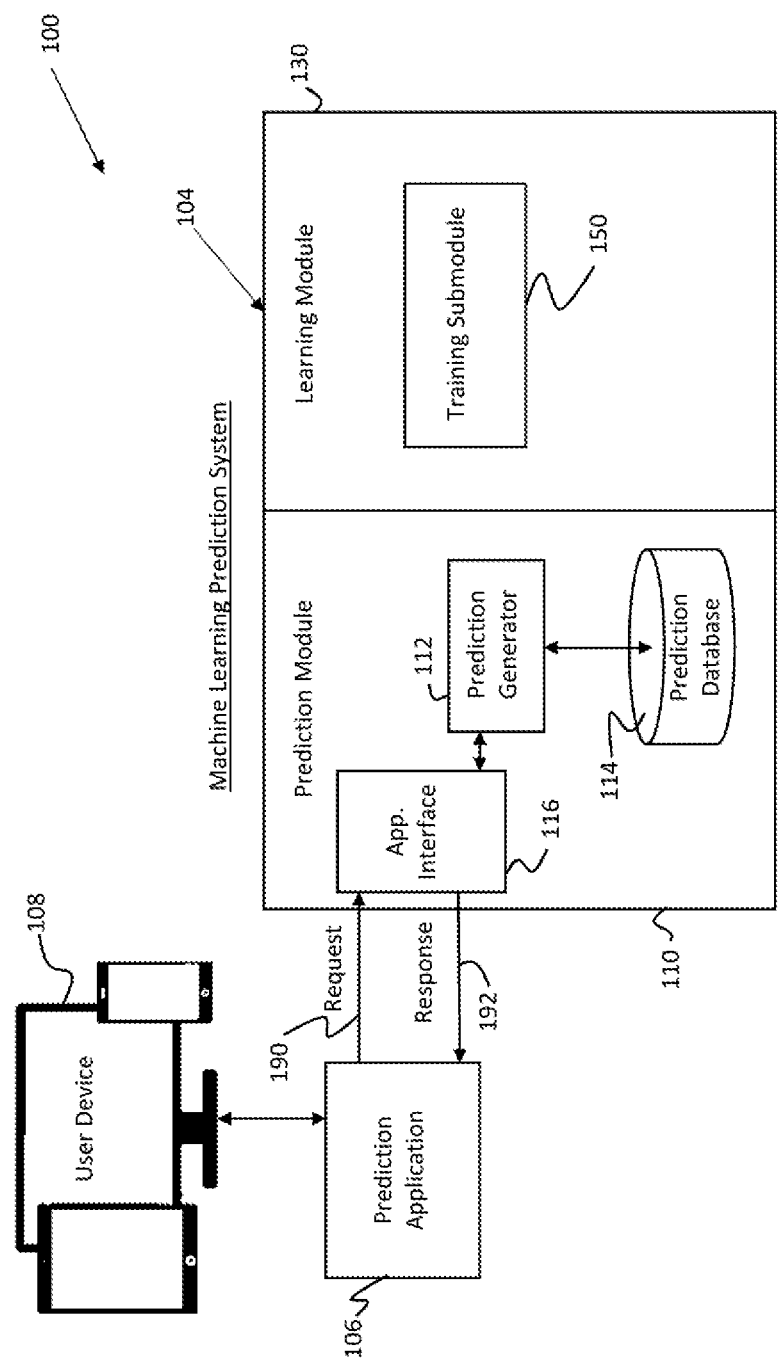
FIG. 4 schematically illustrates various aspects of a computer network architecture including a machine learning prediction system according to various embodiments described herein.

FIG. 4 illustrates operation of the prediction module 110 with respect to processing a prediction request according to various embodiments. An end user may access the machine learning system 104 with a user device 108 via a prediction application 106 (a web application) and request a report. In the request, the end user may provide specific episode data, e.g., specific patient data (patient metrics and treatment), to populate a selected episode profile or template in a selected web application associated with the prediction application 106. The web application may be specific to the request report, e.g., a response such as a prognosis or predicted outcome based on the provided episode data. The prediction application 106 may include other web applications that may provide other reports, e.g., possible treatments, probability of each possible result of each choice, economics, or schedule of prognosis and treatment. The web application may then automatically access the machine learning prediction system 104 and transmit the episode data with the request, as indicated by arrow 190. The prediction module 110 may include an application interface 116 configured to handle communication between the prediction application 106 and the prediction module 110.

The request may be provide to a prediction generator 112 to generate the requested response. Using the desired response specified in the report request and available episode data, the prediction generator 112 selects the appropriate model in the prediction database 114. An identified client model may also be used. The prediction generator 112 may then execute the selected model utilizing the episode data specified in the request to generate a prediction response for the specified outcome in the request. The prediction module 110 may then provide the requested report including the prediction response, indicated by arrow 192, to the prediction application 106, via the application interface 116, for presentation to the user with the user device 108.

Prediction Architecture

Figure 5:
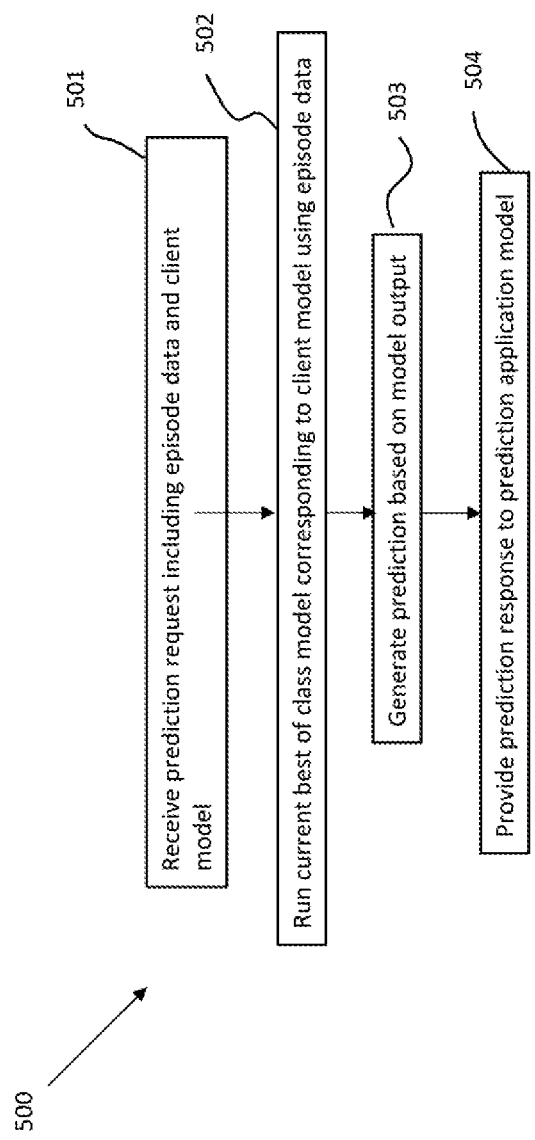
FIG. 5 is a training process of a machine learning prediction system according to various embodiments described herein.

FIG. 5 illustrates a prediction process 500 that may be utilized by the machine learning prediction system 104 (see, e.g., FIGS. 1, 2, & 4) according to various embodiments. The process 500 includes receiving a prediction request 501. As described above with respect to FIG. 4, the prediction request may include a request for a report and include specific episode data and identify a client model. Using the episode data and best in class model in the prediction database corresponding to the client model, the episode data may be input into the model and model may be run 502. The running of the model with the episode data generates a prediction response based on the model output 503. The prediction response may then be provided to the client requester 504, e.g., the prediction module may transmit the response to the prediction application for display, storage, or routing to the user device or another location specified by the client user or request.

Further Machine Learning Architecture

Figure 6:
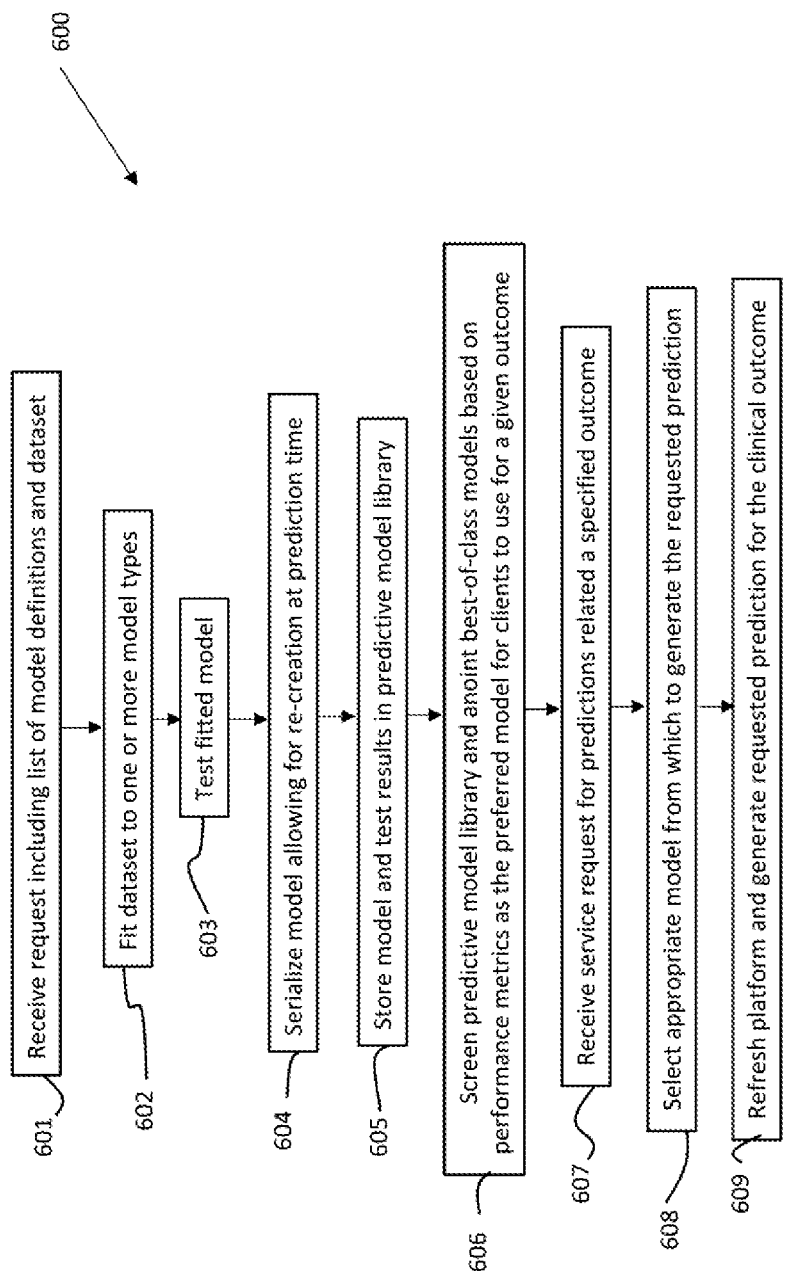
FIG. 6 is a training and prediction process of a computer network architecture including a machine learning prediction system according to various embodiments described herein.

FIG. 6 illustrates a training and prediction process 600 that may be utilized by the machine learning prediction system 104 (see, e.g., FIGS. 1, 2, & 4), according to various embodiments. The process 600 may include receiving a request including a list of model definitions and a dataset 601. The request may be automatically generated, submitted by a system administrator similar to FIG. 2, or submitted by a customer user. The model definition may include identifying data, parameters, or criteria for a modeling protocol. For example, the request may specify a training dataset, outcomes to model, and factors that should be used to power the model. The dataset may then be fit to one or more model types, which may include multiple models corresponding to a single model type, based on the model definitions 602. The fitted model may then be tested, which may include estimating in and out of sample error 603. As described with respect to FIG. 2, testing may include cross-validation such as k-fold cross-validation (e.g., 5-fold cross-validation). Following testing, the model may be serialize or otherwise summarized in a way that allows for re-creation at prediction time 604. The model and test results may be stored in the predictive model library 605. The process may further include screening the predictive model library and anointing best-of-class models based on performance metrics as the preferred model for clients to use for a given prediction response request 606.

The process may further include receiving service requests for predictions relating to a specified clinical outcome 607. Next, cased on the client request, a selection of the appropriate model from which to generate the requested prediction response may be made 608. With the appropriate model selected, the next step may include refresh/generate requested predictions for the clinical outcomes 609.

Components of an Architecture

Figure 7:
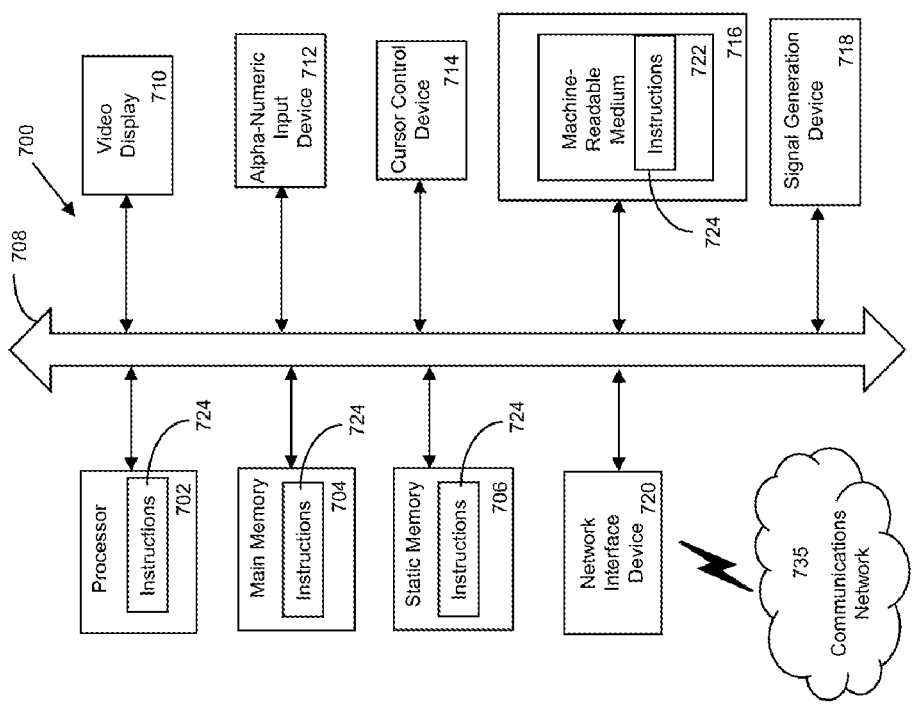
FIG. 7 schematically illustrates components of a system according to various embodiments described herein.

Referring to FIG. 7, at least a portion of the present invention may incorporate one or more computer apparatuses 700. Such a computer apparatus 700 may comprise a machine such as, but not limited to, a computer system, apparatus, or other arrangement of one or more computing devices within which a set of instructions 724, when executed, may cause the machine to perform any one or more of the methodologies or functions discussed above alone or in conjunction other one or more additional machines associated with the network or system, e.g., network architecture 100 or machine learning prediction system 104 described herein, or another network or system. While a single machine 701 is illustrated in FIG. 7, the term "machine" shall also be taken to include any collection of machines that individually or jointly execute a set (or multiple sets) of instructions 724 to perform any one or more of the methodologies discussed herein. The machine may be configured to facilitate various operations conducted by the system. For example, the machine may be configured to, but is not limited to, assist the network or system by providing processing power to assist with processing loads experienced in the network or system, by providing storage capacity for storing instructions 724 or data traversing the network system, or by assisting with any other operations conducted by or within the network or system.

In some embodiments, the computer apparatus 700 or a machine thereof may operate as a standalone device. In some embodiments, the computer apparatus 700 or a machine 701 thereof may be connected via a communication network 735 to and assist with operations performed by other apparatuses, machines, or systems. For example, the computer apparatus 700 or a machine 701 thereof may be connected with any component in the network or system. In a networked deployment, the computer apparatus 700 or a machine thereof may operate in the capacity of a server, server stack, or a client, such as a client user machine, in a server-client user network environment, or as a peer machine in a peer-to-peer (or distributed) network environment. The computer apparatus 701 or a machine thereof may comprise a server computer, a client user computer, a personal computer (PC), a tablet PC, a laptop computer, a desktop computer, a control system, a network router, switch or bridge, or any machine capable of executing a set of instructions 724 (sequential or otherwise) that specify actions to be taken by that computer apparatus 700 or a machine 701 thereof. In one example, the computer apparatus 700 comprising one or more machines 701 is arranged to have a distributed architecture employing a suitable model such as a client-server model. In one embodiment, the computer apparatus 700 may include a web service, e.g., service oriented architecture (SOA) or simple object access protocol (SOAP). The computer apparatus 700 may include a software as a service (SaaS) platform. The computer apparatus 700 may include representational state transfer style resources or resource oriented architecture (ROA). The computer apparatus 700 may include one or more processors, servers, databases, networks or network devices, and peripherals configured to obtain and transmit data and initiate operations configured to perform in whole or in part the operations of the system or platform thereof.

The computer apparatus 700 may include a processor 702, e.g., a central processing unit (CPU), a graphics processing unit (GPU, or both), a main memory 704 and a static memory 706, which communicate with each other via a bus 708. The computer apparatus 700 may further include a video display unit 710, which may be, but is not limited to, a liquid crystal display (LCD), a flat panel, a solid state display, or a cathode ray tube (CRT). The computer apparatus 700 may include an input device 712, such as, but not limited to, a keyboard, a cursor control device 714, such as, but not limited to, a mouse, a disk drive unit 716, a signal generation device 718, such as, but not limited to, a speaker or remote control, and a network interface device 720.

The disk drive unit 716 may include a machine-readable medium 722 on which is stored one or more sets of instructions 724, such as, but not limited to, software embodying any one or more of the methodologies or functions described herein, including those methods illustrated above. For example, the learning or training submodule 130, 150 described herein may include messaging or queuing processes or functions. Thus, the learning or training submodule may include Kue library to handle task distribution and coordination between worker process submodules, which may be backed by Redis in-memory key-value store with pub/sub. The instructions 724 may also reside, completely or at least partially, within the main memory 704, the static memory 706, or within the processor 702, or a combination thereof, during execution thereof by the computer system 700. The main memory 704 and the processor 702 also may constitute machine-readable media.

DESCRIPTION OF PATIENT RISK SCORING
WEB APPLICATION—LAYER 2

The patient risk profile is a form of prediction. That is, the risk of any specific patient outcome is a prediction of the likelihood of that outcome. The patient risk scoring profile may indicate a probability of occurring for each possible outcome of interest for that patient for that episode type, such as durations, medical outcomes, financial parameters (e.g. costs), and other metrics.

Described here are computer network architectures for machine learning, and more specifically, to computer network architectures to forecast the probabilities of the various possible outcomes of patient treatment, in the context of program rules using combinations of defined patient clinical episode metrics and clinical financial metrics.

Program rules may be the rules of payor programs for treatment, such as Medicaid and Medicare rules, and of private payor programs by insurance companies or other payors, or programs that combine medical service with payment of costs, such as the federal Veterans Administration or combined private programs. The rules may be for specific treatment episode types (such as, e.g., a knee replacement or a coronary bypass), and may control factors such as the specific content of care, what drugs to use, duration of in-patient care, costs, cost caps, and bonuses or penalties for the service providers pursuant to program rules for certain performance parameters.

Patient clinic episode metrics may include, e.g., duration of inpatient care, duration of outpatient care, success of treatment, morbidity of the patient, readmission of the patient, side effects of treatment, and others.

Clinic financial metrics may include, e.g., total cost of care, cost of medical services, cost of drugs, bonuses and penalties charged to the service provider for performance under program rules, and others.

Forecasts of the probabilities of various possible outcomes of patient treatment are often referred to as patient risk scores or patient risk scoring.

The following is an example of the work flow of an embodiment of the present invention for a user experience with the embodiment:
1. Receive a user prediction request for patient risk scoring, for a patient, for a specific clinical episode type.
2. Transmit the user prediction request for patient risk scoring to the prediction module.
3. Automatically calibrate the correlation of demographic, social and medical attributes of the patient, to the outcome of specific patient clinical episode types.
4. Combine data of patient interactions with the healthcare team and proprietary third-party patient attributes data into model attributes.
5. Produce an interpretable schedule, adjusted for program rules, of the marginal impact of patient attributes on the outcomes of the patient episode.

Embodiments automatically use the pipeline of healthcare outcome models to select and apply the optimal predictive model for patient risk scores specific to certain patient clinical episode definitions.

In an embodiment, a computer network architecture with patient risk scoring, artificial intelligence and machine learning, comprises (1) a prediction module with a prediction generator and an updated database, (2) a learning module with a training submodule, in electronic communication with the prediction module and the updated database, (3) a web application in electronic communication with both the prediction module, and a user device, and wherein, (4) the web application is adapted to:
 a. Receive a user prediction request for patient risk scoring, for a patient, for a specific clinical episode type,
 b. Transmit the user prediction request for patient risk scoring to the prediction module,
 c. Automatically calibrate the correlation of demographic, social and medical attributes of the patient, to the outcome of specific patient clinical episode types to be analyzed,
 d. Combine data of patient interactions with the healthcare team and proprietary third-party patient attributes data into model attributes.
 e. Produce an interpretable schedule, adjusted for program rules, of the marginal impact of patient attributes on the outcomes of the patient episode.

In various embodiments, in FIG. 3, the request 301,501, 601 may be a request to select a preferred model to predict the patient risk profile 306,606. In FIGS. 5 and 6, the prediction request 301,607 may be a request to predict a patient risk profile. The requested prediction generated may be the requested patient risk profile generated 609.

In various embodiments, FIG. 3 and FIG. 6, the model definition and data sets 301,601 may be for patient risk scoring models and data. And the episode data and client model 501 may be episode data and client models for patient risk scoring.

In various embodiments, the prediction application 106 in FIG. 1 and FIG. 9 may be embodied by the patient risk scoring web application 806,906 in FIG. 8 and FIG. 9.

Figure 10:
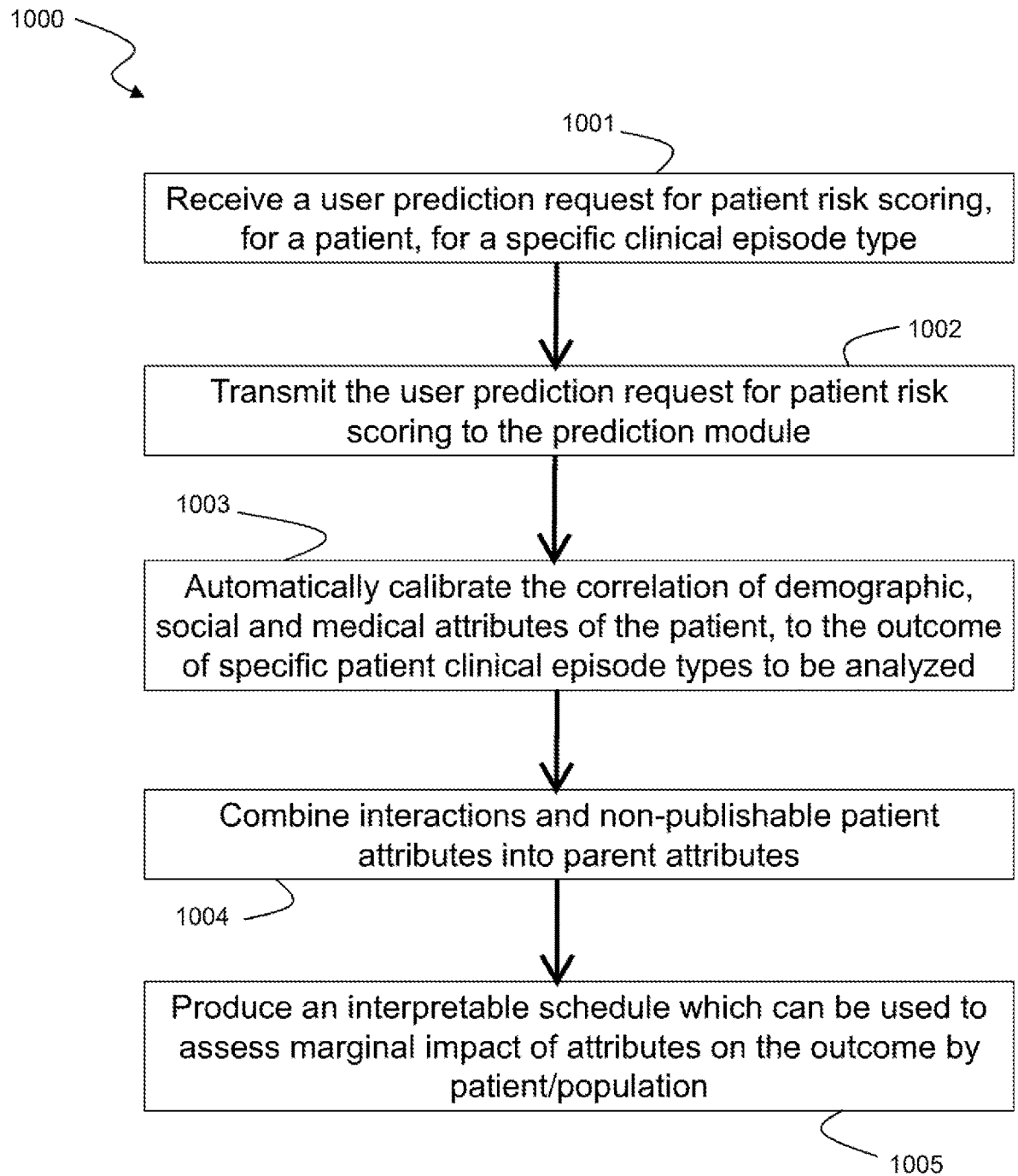
FIG. 10 Is a process for a patient risk scoring web application according to various embodiments described herein.

The process 1000 for the patient risk scoring web application 806,906, according to various embodiments, is shown in FIG. 10. The patient risk scoring web application 806 receives 1001 a user prediction request for patient risk scoring for a patient, for a specific clinical episode type. The user creates this prediction request through a user device 108 that accesses the web application 806.

The web application 806, 906 may then transmit 1002 the user prediction request 190 for patient risk scoring to the prediction module 110. The prediction module may then access the learning module 130 to automatically calibrate 1003 (or recalibrate) the correlation of demographic, social and medical attributes of the patient, to the outcome of the specific patient clinical episode types to be analyzed, and select the optimal model for the prediction from the available choices. Alternatively, the prediction module may use a previously calibrated and selected optimal model for the request. If the models have already been calibrated, the step may recalibrate and update the models with an expanded database that has been expanded since the last update of the correlations.

The web application 906 may combine 1004 data of patient interactions with the healthcare team and with the present invention, and proprietary third-party patient attributes data and model attributes. All patient data from all sources is kept in the various databases 114, 132, 152 of the present invention. Each prediction request 190 collects data for at least one patient, which is added to the databases with each request. As described herein, the databases are also augmented with new data by administrators 108, through an administrator application 172. Each patient interaction with the system 100 through some other web application 106, such as a dynamic patient guidance application 106, or other interaction with the healthcare team such as a doctor visit, may also add data to the databases. Also, proprietary data from third party vendors about patient data for medical, financial, economic, and other data may be added to the databases. Individual data from whatever source is treated confidentially, and is not disclosed; however, the data can be aggregated across demographic groups, and also used to calculate derivative data, all of which can be used as data for the variables in the functional equations of optimal prediction models. The patient risk scoring requested may then be disclosed to the individual patient and his clinician, without disclosing any confidential data of any other individual.

A Focus of the Robot's Intelligence and Learning

This ongoing updating and recalibration of the optimal forecasting model using augmented data in 1003 and 1004 is an important source of machine learning (i.e., artificial intelligence) in embodiments. One indicia of artificial intelligence and machine learning is that when the system receives the same user request on two different days, the response on the second day will be different and smarter because the database has been expanded (i.e., the machine has learned), and the answer will be more accurate because the model is recalibrated with more data (i.e., the intelligence of the machine is increased). Because data is augmented in part from the machine's own receipt of user requests (i.e., each request with more patient data is added to the system databases), the machine is learning from its own experience and use. The more the computer architecture experiences, the more the computer architecture learns, because it incorporates more data.

The web application 906 may then use the resulting data to produce 1005 an interpretable schedule, adjusted by program rules, of the impact of attributes in the patient risk profile on the outcomes of the patient clinical episode. The interpretable schedule is a schedule of the forecasted risk (i.e., probability) of each parameter of each possible patient episode outcome of interest for the patient's risk scoring request. The schedule is interpretable because it includes some aggregate statistics and information about the large database used to calibrate and run the prediction model. (No confidential individual data is disclosed to the requesting user). For example, the size, average age, average family income, and gender of the large database used to drive the projection might be indicated, to allow the clinician of the patient in the user request to evaluate and interpret the resulting risk profile based on his own judgment. Hence, the risk profile is interpreted considering the patient population demographic groups used to calibrate the model and forecast the risks, and distinguished by demographic parameters of the patient of the request.

In various embodiments, the interpretable schedule may assess the marginal impact of patient attributes on the outcome of parameters of the patient clinical episode. For example, a correlation of patient attributes to clinical episode outcomes in a multiple regression to calibrate and select a forecasting model, also may yield cross-elasticities (i.e., sensitivities) of patient attributes to episode outcomes. This cross-elasticity or sensitivity measures the marginal impact of patient attributes to episode outcomes.

Another unique improvement of various embodiments is that the interpretable schedule reflects outcomes and probabilities (i.e., risks) after adjustment for medical program rules. For example, the total cost of episode treatment is predicted for the total cost after adjustment for program rules for payment caps on total costs, and the resulting payment of bonuses to, or the receipt of penalties from, service providers.

Other Matters

Although various embodiments may be referred to as robots because of their machine learning and artificial intelligence, these embodiments might not have an anthropomorphic form or sound.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example network or system is applicable to software, firmware, and hardware implementations.

In accordance with various embodiments of the present disclosure, the processes described herein are intended for operation as software programs running on a computer processor. Furthermore, software implementations can include, but are not limited to, distributed processing or component/object distributed processing, parallel processing, or virtual machine processing that may be constructed to implement the methods described herein.

The present disclosure describes various modules, which may also be referred to as sub-modules, generators, engines, systems, subsystems, components, units, and the like. Such modules may include functionally related hardware, instructions, firmware, or software. Modules may include physical or logical grouping of functionally related applications, services, resources, assets, systems, programs, databases, or the like. Modules or hardware storing instructions or configured to execute functionalities of the modules may be physically located in one or more physical locations. For example, modules may be distributed across one or more networks, systems, devices, or combination thereof. It will be appreciated that the various functionalities of these features may be modular, distributed, and/or integrated over one or more physical devices. While the learning database as well as the training databases are illustrated individually as discrete elements, it will be appreciated that such logical partitions may not correspond to physical partitions of the data. For example, all or portions of the databases may reside or be distributed among one or more hardware locations. Further, while screening for best-of-class or current best model is generally described as including scanning the predictive model library 142, this library 142 includes the models currently used by the prediction module 110, references to such models, evaluation metrics related to such data, or other data from which the screening may be performed to properly screen the library 142 of predictive models for the best-of-class or current best model.

The present disclosure contemplates a machine-readable medium 722 containing instructions 724 so that a device connected to the communications network 735, another network, or a combination thereof, can send or receive voice, video or data, and to communicate over the communications network 735, another network, or a combination thereof, using the instructions. The instructions 724 may further be transmitted or received over the communications network 735, another network, or a combination thereof, via the network interface device 720.

While the machine-readable medium 722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of the network architecture, systems, and processes that might make use of the structures described herein. While the present disclosure generally describes the inventive network architecture, systems, and process with respect to healthcare applications, the healthcare field is but only one of many potential applications. Indeed, those having skill in the art will appreciate that the network architecture, systems, and processes described herein may find application in many industries. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

What is claimed is:

1. A method that utilizes artificial intelligence and machine learning, comprising:
    logging a patient into a dynamic patient guidance web application (DPGWA) in electronic communication with both a prediction module and a user device,
    receiving, by the DPGWA, data from the patient about the patient behavior and/or compliance with a patient care plan,
    logging the patient out of the DPGWA,
    automatically re-scoring, by the DPGWA, the patient's risk scores by accessing a patient risk scoring web application,
    based on the new risk scores, updating, by the DPGWA, the patient care plan,
    sending, by the DPGWA, an automated message for the patient to the user mobile device requesting that the patient complete a check-in with the DPGWA and receive the updated patient care plan,
    creating, by the DPGWA, a reminder task for a patient clinical care coordinator to contact the patient, if the patient has not responded within a time period,
    if the patient has a designated caregiver, sending, by the DPGWA, a notification to the designated caregiver either (1) to prompt the patient to respond or (2) to respond on behalf of the patient to provide patient check-in information, and receive the updated patient care plan, and
    if the patient adheres to their patient care plan, reducing, by the DPGWA, the cadence of interventions by a care coordinator for that patient,
    receiving, by a learning module with a training submodule and in electronic communication with a prediction module and an updated database, a list of algorithm definitions and datasets for patient risk scoring,
    automatically calibrating, by the learning module, one or more defined algorithms with the database, testing, by the learning module, the calibrated algorithms with a plurality of evaluation metrics,
storing, by the learning module, the calibrated algorithms and evaluation metrics in a library,
automatically selecting, by the learning module, an algorithm for patient risk scoring based on the evaluation metrics,
updating, by the learning module, further the database with third party data, and with user episode data, and
re-executing, by the learning module, the calibrate, test, store, and select steps after the update of the database step,
receiving, by the prediction module with a prediction generator, a user prediction request for patient risk scoring, including episode data and a client model,
running, by the prediction module, the currently selected algorithm corresponding to the user of the episode data, and generating patient risk scoring prediction output,
generating, by the prediction module, a patient risk scoring prediction report based on the algorithm output, and
transmitting, by the prediction module, the patient risk scoring prediction report to the user,
wherein, the algorithm definitions are of types that are members of the group comprising:
multi-level models,
random forest regression,
logistical regression,
gamma-distributed regression, and
linear regression;
the third party data is from a party that is a member of the group comprising:
hospitals,
medical practices,
insurance companies,
credit reporting agencies, and
credit rating agencies;
the database includes patient medical data, patient personal data, patient outcome data, and medical treatment data;
the episode data includes individual patient medical data and personal data; and
the user is a member of the group comprising:
hospitals,
medical practices, and
insurance companies,
wherein the user device is remote from the prediction module, and the user device is a member of the group comprising:
a computer,
a desktop PC,
a laptop PC,
a smart phone,
a tablet computer, and
a personal wearable computing device,
wherein the web application communicates with the user device by the Internet, or an extranet, or a VPN, or other network, and the web application is generic for any user, or customized for a specific user, or class of user, and
wherein, the user prediction request requests calibration of the correlation of demographic, social and medical attributes of the patient, to the outcome of a specific patient clinical episode type.

2. A method that utilizes artificial intelligence and machine learning, comprising:
logging a patient into a dynamic patient guidance web application (DPGWA) in electronic communication with a prediction module, a patient risk scoring web application, and a user device, wherein the prediction module has a prediction generator and an updated database, wherein the prediction module is in electronic communication with a learning module with a training submodule,
receiving, by the DPGWA, data from the patient about the patient behavior and/or compliance with a patient care plan,
logging the patient out of the DPGWA,
automatically re-scoring, by the DPGWA, the patient's risk scores by accessing the patient risk scoring web application,
based on the new risk scores, updating, by the DPGWA, the patient care plan,
sending, by the DPGWA, an automated message for the patient to the user mobile device requesting that the patient complete a check-in with the DPGWA and receive the updated patient care plan,
creating, by the DPGWA, a reminder task for a patient clinical care coordinator to contact the patient, if the patient has not responded within a time period,
if the patient has a designated caregiver, sending, by the DPGWA, a notification to the designated caregiver either (1) to prompt the patient to respond or (2) to respond on behalf of the patient to provide patient check-in information, and receive the updated patient care plan, and
if the patient adheres to their patient care plan, reducing, by the DPGWA, the cadence of interventions by a care coordinator for that patient.

3. The method of claim 2, further comprising:
receiving, by the learning module, a list of algorithm definitions and datasets for patient risk scoring,
automatically calibrating, by the learning module, one or more defined algorithms with the database,
testing, by the learning module, the calibrated algorithms with a plurality of evaluation metrics,
storing, by the learning module, the calibrated algorithms and evaluation metrics in a library,
automatically selecting, by the learning module, an algorithm for patient risk scoring based on the evaluation metrics,
updating, by the learning module, further the database with third party data, and with user episode data, and
re-executing, by the learning module, the calibrate, test, store, and select steps after the update of the database step.

4. The method of claim 2, further comprising:
receiving, by the prediction module with a prediction generator, a user prediction request for patient risk scoring, including episode data and a client model,
running, by the prediction module, the currently selected algorithm corresponding to the user of the episode data, and generating patient risk scoring prediction output,
generating, by the prediction module, a patient risk scoring prediction report based on the algorithm output, and
transmitting, by the prediction module, the patient risk scoring prediction report to the user.

5. The method of claim 2, wherein:
the algorithm definitions are of types that are members of the group comprising:
multi-level models,
random forest regression,
logistical regression,
gamma-distributed regression, and
linear regression;

the third party data is from a party that is a member of the group comprising:
hospitals,
medical practices,
insurance companies,
credit reporting agencies, and
credit rating agencies;
the database includes patient medical data, patient personal data, patient outcome data, and medical treatment data;
the episode data includes individual patient medical data and personal data; and
the user is a member of the group comprising:
hospitals,
medical practices, and
insurance companies.

6. The method of claim 2, wherein the user device is remote from the prediction module, and the user device is a member of the group comprising:
a computer,
a desktop PC,
a laptop PC,
a smart phone,
a tablet computer, and
a personal wearable computing device.

7. The method of claim 2, wherein the web application communicates with the user device by the Internet, or an extranet, or a VPN, or other network, and the web application is generic for any user, or customized for a specific user, or class of user, and
wherein, the user prediction request requests calibration of the correlation of demographic, social and medical attributes of the patient, to the outcome of a specific patient clinical episode type.

8. A method that utilizes a web application for artificial intelligence and machine learning, comprising:
logging a patient into a dynamic patient guidance web application (DPGWA) in electronic communication with a prediction module, a patient risk scoring web application, and a user device,
receiving, by the DPGWA, data from the patient about the patient behavior and/or compliance with a patient care plan,
logging the patient out of the DPGWA,
automatically re-scoring, by the DPGWA, the patient's risk scores by accessing the patient risk scoring web application,
based on the new risk scores, updating, by the DPGWA, the patient care plan,
sending, by the DPGWA, an automated message for the patient to the user mobile device requesting that the patient complete a check-in with the DPGWA and receive the updated patient care plan,
creating, by the DPGWA, a reminder task for a patient clinical care coordinator to contact the patient, if the patient has not responded within a time period,
if the patient has a designated caregiver, sending, by the DPGWA, a notification to the designated caregiver either (1) to prompt the patient to respond or (2) to respond on behalf of the patient to provide patient check-in information, and receive the updated patient care plan, and
if the patient adheres to their patient care plan, reducing, by the DPGWA, the cadence of interventions by a care coordinator for that patient,
receiving, by a learning module with a training submodule and in electronic communication with a prediction module and an updated database, a list of algorithm definitions and datasets for patient risk scoring, automatically calibrating, by the learning module, one or more defined algorithms with the database,
testing, by the learning module, the calibrated algorithms with a plurality of evaluation metrics,
storing, by the learning module, the calibrated algorithms and evaluation metrics in a library,
automatically selecting, by the learning module, an algorithm for patient risk scoring based on the evaluation metrics,
updating, by the learning module, further the database with third party data, and with user episode data, and
re-executing, by the learning module, the calibrate, test, store, and select steps after the update of the database step,
receiving, by a prediction generator of the prediction module, a user prediction request for patient risk scoring, including episode data and a client model,
running, by the prediction generator, the currently selected algorithm corresponding to the user of the episode data, and generating patient risk scoring prediction output,
generating, by the prediction generator, a patient risk scoring prediction report based on the algorithm output, and
transmitting, by the prediction generator, the patient risk scoring prediction report to the user,
wherein, the algorithm definitions are of types that are members of the group comprising:
multi-level models,
random forest regression,
logistical regression,
gamma-distributed regression, and
linear regression;
the third party data is from a party that is a member of the group comprising:
hospitals,
medical practices,
insurance companies,
credit reporting agencies, and
credit rating agencies;
the database includes patient medical data, patient personal data, patient outcome data, and medical treatment data;
the episode data includes individual patient medical data and personal data; and
the user is a member of the group comprising:
hospitals,
medical practices, and
insurance companies,
wherein, the user device is remote from the prediction module, and
the user device is a member of the group comprising:
a computer,
a desktop PC,
a laptop PC,
a smart phone,
a tablet computer, and
a personal wearable computing device,
wherein the web application communicates with the user device by the Internet, or an extranet, or a VPN, or other network, and the web application is generic for any user, or customized for a specific user, or class of user, and
wherein, the user prediction request requests calibration of the correlation of demographic, social and medical attributes of the patient, to the outcome of a specific patient clinical episode type.

9. A method that utilizes a dynamic patient guidance web application with artificial intelligence and machine learning, comprising:
  logging a patient into a dynamic patient guidance web application (DPGWA) in electronic communication with a prediction module, a patient risk scoring web application, and a user device,
  receiving, by the DPGWA, data from the patient about the patient behavior and/or compliance with a patient care plan,
  logging the patient out of the DPGWA,
  automatically re-scoring, by the DPGWA, the patient's risk scores by accessing the patient risk scoring web application,
  based on the new risk scores, updating, by the DPGWA, the patient care plan,
  sending, by the DPGWA, an automated message for the patient to the user mobile device requesting that the patient complete a check-in with the DPGWA and receive the updated patient care plan,
  creating, by the DPGWA, a reminder task for a patient clinical care coordinator to contact the patient, if the patient has not responded within a time period,
  if the patient has a designated caregiver, sending, by the DPGWA, a notification to the designated caregiver either (1) to prompt the patient to respond or (2) to respond on behalf of the patient to provide patient check-in information, and receive the updated patient care plan, and
  if the patient adheres to their patient care plan, reducing, by the DPGWA, the cadence of interventions by a care coordinator for that patient.

10. The method of claim 9, further comprising:
  receiving, by a learning module with a training submodule and in electronic communication with the prediction module and an updated database, a list of algorithm definitions and datasets for patient risk scoring,
  automatically calibrating, by the learning module, one or more defined algorithms with the database,
  testing, by the learning module, the calibrated algorithms with a plurality of evaluation metrics,
  storing, by the learning module, the calibrated algorithms and evaluation metrics in a library,
  automatically selecting, by the learning module, an algorithm for patient risk scoring based on the evaluation metrics,
  updating, by the learning module, further the database with third party data, and with user episode data, and
  re-executing, by the learning module, the calibrate, test, store, and select steps after the update of the database step.

11. The method of claim 9, further comprising:
  receiving, by a prediction generator of the prediction module, a user prediction request for patient risk scoring, including episode data and a client model,
  running, by the prediction generator, the currently selected algorithm corresponding to the user of the episode data, and generating patient risk scoring prediction output,
  generating, by the prediction generator, a patient risk scoring prediction report based on the algorithm output, and
  transmitting, by the prediction generator, the patient risk scoring prediction report to the user.

12. The method of claim 9, wherein:
  the algorithm definitions are of types that are members of the group comprising:
    multi-level models,
    random forest regression,
    logistical regression,
    gamma-distributed regression, and
    linear regression;
  the third party data is from a party that is a member of the group comprising:
    hospitals,
    medical practices,
    insurance companies,
    credit reporting agencies, and
    credit rating agencies;
  the database includes patient medical data, patient personal data, patient outcome data, and medical treatment data;
  the episode data includes individual patient medical data and personal data; and
  the user is a member of the group comprising:
    hospitals,
    medical practices, and
    insurance companies.

13. The method of claim 9,
  wherein the user device is remote from the prediction module, and the user device is a member of the group comprising:
    a computer,
    a desktop PC,
    a laptop PC,
    a smart phone,
    a tablet computer, and
    a personal wearable computing device.

14. The method of claim 9, wherein the web application communicates with the user device by the Internet, or an extranet, or a VPN, or other network, and the web application is generic for any user, or customized for a specific user, or class of user, and
  wherein, the user prediction request requests calibration of the correlation of demographic, social and medical attributes of the patient, to the outcome of a specific patient clinical episode type.

* * * * *